(12) United States Patent
Wang et al.

(10) Patent No.: US 7,705,158 B2
(45) Date of Patent: Apr. 27, 2010

(54) INHIBITORS OF ION CHANNELS

(75) Inventors: Xiaodong Wang, Chapel Hill, NC (US); Alan Fulp, Willow Springs, NC (US); Brian Marron, Durham, NC (US); Serge Beaudoin, Cary, NC (US); Darrick Seconi, Cary, NC (US); Mark Suto, Chapel Hill, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 11/555,977

(22) Filed: Nov. 2, 2006

(65) Prior Publication Data

US 2007/0135493 A1 Jun. 14, 2007

Related U.S. Application Data

(60) Provisional application No. 60/732,543, filed on Nov. 2, 2005.

(51) Int. Cl.
*A61K 31/427* (2006.01)
*C07D 277/46* (2006.01)
(52) U.S. Cl. ...................... 548/195; 514/371
(58) Field of Classification Search ............. 546/273.1; 548/195; 514/371
See application file for complete search history.

(56) References Cited

U.S. PATENT DOCUMENTS 2,826,594 A * 3/1958 Dreisbach .................... 564/79
6,576,791 B1 6/2003 Axt et al.

FOREIGN PATENT DOCUMENTS

JP 08231505 A * 9/1996
JP 2000309534 A * 11/2000

OTHER PUBLICATIONS

Gheorghiu, C. V.; Budeanu, C.; Budeanu, Elena; Toma, A. "Sulfonamides. V. The antituberculous action of certain new thioureas, sulfonamide derivatives, and of aromatic amino acids." Acad. rep. Populare Romine, studii cercetari chim., 1956, 4 (No. 1-2), 47-56. (Abstract only).*
Badawi, A. M.; Harfoush, A. A.; Shalaby, A.; Abdel-Rahman, T. M. "Studies on amebicidal agents: II. Synthesis and amebicidal activity of toluene-2,4-bis-sulfon-N-anilides." Oriental Journal of Chemistry, 1986, 2(1), 40-4 (abstract only).*
Shams, N. A.; Donia, S. G.; El-Rahman, T. M. Abd "Synthesis and reactions of aryl-2,4-bis(sulfonyl azides)." Journal of the Chemical Society of Pakistan, 1986, 8(2), 209-16 (Abstract only).*
Dorwald F. A. Side Reactions in Organic Synthesis, 2005, Wiley: VCH, Weinheim p. IX of Preface pp. 1-15.*
"Isopentyl Nitrite" Encyclopedia of Reagents for Organic Synthesis online "http://www.mrw.interscience.wiley.com/eros/articles/ri074/sect0-fs.html" Nov. 27, 2007.*
Ok et. al. "Synthesis and SAR of 1,2-trans-(1-hydroxy-3-phenylprop-1-yl) cyclopentane carboxamide derivatives, a new class of sodium channel blockers" Bioorganic & Medicinal Chemistry Letters 2006, 16, 1358-1361.*
Gheorghiu, C. V.; Budeanu, C.; Budeanu, Elena; Toma, A. "Sulfonamides. V. The antituberculous action of certain new thioureas, sulfonamide derivatives, and of aromatic amino acids." Acad. rep. Populare Romine, studii cercetari chim., 1956, 4(No. 1-2), 47-56.*
In the Pipeline, online, accessed Jun. 16, 2008, "http://pipeline.corante.com/archives/2006/01/24/the_examiner_finally_snaps.php".*

* cited by examiner

*Primary Examiner*—Rita J Desai
*Assistant Examiner*—David K. O'Dell
(74) *Attorney, Agent, or Firm*—Townsend and Townsend and Crew LLP

(57) ABSTRACT

Compounds, compositions and methods are provided which are useful in the treatment of diseases through the inhibition of sodium ion flux through voltage-gated sodium channels. More particularly, the invention provides substituted aryl sulfonamides, compositions comprising these compounds, as well as methods of using these compounds or compositions in the treatment of central or peripheral nervous system disorders, particularly pain and chronic pain by blocking sodium channels associated with the onset or recurrence of the indicated conditions. The compounds, compositions and methods of the present invention are of particular use for treating neuropathic or inflammatory pain by the inhibition of ion flux through a voltage-gated sodium channel.

31 Claims, No Drawings

INHIBITORS OF ION CHANNELS

CROSS REFERENCE TO RELATED APPLICATIONS

This application claims priority to U.S. Provisional Patent Application Ser. No. 60/732,543, filed on Nov. 2, 2005, which is herein incorporated by reference in its entirety for all purposes.

FIELD OF THE INVENTION

This invention relates to the use of certain compounds as sodium channel blockers and to the treatment of pain by the inhibition of sodium channels. Additionally, this invention relates to novel compounds that are useful as sodium channel blockers.

BACKGROUND OF THE INVENTION

Voltage-gated sodium channels are found in all excitable cells including myocytes of muscle and neurons of the central and peripheral nervous system. In neuronal cells sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (See Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)). See Table I, below.

3(3): 173-9 (2003)). Consequently, blockers of $Na_v1.5$ have found clinical utility in treatment of such disorders (Srivatsa U, et al., *Curr. Cardiol. Rep.*, 4(5): 401-10 (2002)). The remaining TTX-resistant sodium channels, $Na_v1.8$ (SCN10A, PN3, SNS) and $Na_v1.9$ (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v1.8$ has been found in the CNS of human multiple sclerosis (MS) patients and also in a rodent model of MS (Black, J A, et al., *Proc. Natl. Acad. Sci. USA,* 97(21): 11598-602 (2000)). Evidence for involvement in nociception is both associative (preferential expression in nociceptive neurons) and direct (genetic knockout). $Na_v1.8$-null mice exhibited typical nociceptive behavior in response to acute noxious stimulation but had significant deficits in referred pain and hyperalgesia (Laird J M, et al., *J. Neurosci.*, 22(19): 8352-6 (2002)).

The TTX-sensitive subset of voltage-gated sodium channels is expressed in a broader range of tissues than the TTX-resistant channels and has been associated with a variety of human disorders. The $Na_v1.1$ channel well exemplifies this general pattern, as it is expressed in both the central and peripheral nervous system and has been associated with several seizure disorders including Generalized Epilepsy with Febrile Seizures Plus, types 1 and 2 (GEFS+1, GEFS+2), Severe Myoclonic Epilepsy of Infancy (SMEI), and others (Claes, L, et al., *Am. J. Hum. Genet.*, 68: 1327-1332 (2001); Escayg, A., *Am. J. Hum. Genet.*, 68: 866-873 (2001); Lossin, C, *Neuron,* 34: 877-884 (2002)). The $Na_v1.2$ channel is largely, if not exclusively, expressed in the central nervous system and quantitative studies indicate it is the most abundant VGSC of the CNS. Mutations of $Na_v1.2$ are also associated with seizure disorders (Berkovic, S. F., et al., *Ann. Neurol.*, 55: 550-557 (2004)) and $Na_v1.2$-null "knockout" mice exhibit perinatal lethality (Planells-Cases R et al., *Biophys. J.,*

TABLE I

| Type | Gene Symbol | Primary tissue | TTX IC-50 | Disease association | Indications |
|---|---|---|---|---|---|
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Sk. muscle | 25 | Myotonia | Myotonia |
| $Na_v1.5$ | SCN5A | Heart | 2000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50000 | — | Pain |
| $Na_v1.9$ | SCN11A | PNS | 1000 | — | Pain |

There are currently 10 known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The $Na_v1.x$ subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue and has been shown to underlie a variety of cardiac arrhythmias and conduction disorders (Liu H, et al., *Am. J. Pharmacogenomics,*

78(6):2878-91 (2000)). Expression of the $Na_v1.4$ gene is largely restricted to skeletal muscle and, accordingly, mutations of this gene are associated with a variety of movement disorders (Ptacek, L. J., *Am. J. Hum. Genet.*, 49: 851-854 (1991); Hudson A J, *Brain,* 118(2): 547-63 (1995)). The majority of these disorders are related to hyperactivity or "gain-of-function" and have been found to respond to treatment with sodium channel blockers (Desaphy J F, et al., *J. Physiol.*, 554(2): 321-34 (2004)).

Neither the SCN3A nor the SCN8A VGSC genes have been conclusively linked to heritable disorders in humans. Loss-of-function mutations of the SCN8A gene are known in mice and yield increasingly debilitating phenotypes, dependent upon the remaining functionality of the gene products (Meisler M H, *Genetica*, 122(1): 37-45 (2004)). Homozygous null mutations cause progressive motor neuron failure leading to paralysis and death, while heterozygous null animals are asymptomatic. Homozygous med$^J$ mice have nearly 90% reduction in functional Na$_v$1.6 current and exhibit dystonia and muscle weakness but are still viable. Evidence for Na$_v$1.6 being important for nociception is largely associative as Na$_v$1.6 is expressed at high levels in dorsal root ganglia and can be found in spinal sensory tracts (Tzoumaka E, *J. Neurosci. Res.*, 60(1): 37-44 (2000)). It should be noted however that expression of Na$_v$1.6 is not restricted to sensory neurons of the periphery. Like the Na$_v$1.6 channel, expression of the Na$_v$1.3 VGSC can also be detected in both the central and peripheral nervous system, though levels in the adult CNS are generally much higher than PNS. During development and the early postnatal period Na$_v$1.3 is expressed in peripheral neurons but this expression wanes as the animal matures (Shah B S, *Physiol.*, 534(3): 763-76 (2001); Schaller K L, *Cerebellum*, 2(1): 2-9 (2003)). Following neuronal insult Na$_v$1.3 expression is upregulated, more closely mimicking the developmental expression patterns (Hains B C, *J. Neurosci.*, 23(26): 8881-92 (2003)). Coincident with the recurrence of Na$_v$1.3 expression is the emergence of a rapidly re-priming sodium current in the injured axons with a biophysical profile similar to Na$_v$1.3 (Leffler A, et al., *J. Neurophysiol.*, 88(2): 650-8 (2002)). Treatment of injured axons with high levels of GDNF has been shown to diminish the rapidly repriming sodium current and reverses thermal and mechanical pain-related behaviors in a rat model of nerve injury, presumably by down-regulating the expression of Na$_v$1.3 (Boucher T J, *Curr. Opin. Pharmacol.*, 1(1): 66-72 (2001)). Specific down-regulation of Na$_v$1.3 via treatment with antisense oligonucleotides has also been shown to reverse pain-related behaviors following spinal cord injury (Hains B C, *J. Neurosci.*, 23(26): 8881-92 (2003)).

The Na$_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows 90% amino acid identity between the human and rat genes (Toledo-Aral et al., *Proc. Natl. Acad. Sci. USA*, 94(4): 1527-1532 (1997)).

An increasing body of evidence suggests that Na$_v$1.7 may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, Na$_v$1.7 protein has been shown to accumulate in neuromas, particularly painful neuromas (Kretschmer et al., *Acta. Neurochir.* (Wien), 144(8): 803-10 (2002)). Mutations of Na$_v$1.7, both familial and sporadic, have also been linked to primary erythermalgia, a disease characterized by burning pain and inflammation of the extremities (Yang et al., *J. Med. Genet.*, 41(3): 171-4 (2004)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433).

Sodium channel-blocking agents have been reported to be effective in the treatment of various disease states, and have found particular use as local anesthetics and in the treatment of cardiac arrhythmias. It has also been reported that sodium channel-blocking agents may be useful in the treatment of pain, including acute, chronic, inflammatory and/or neuropathic pain; see, for example, Wood, J N et al., *J. Neurobiol.*, 61(1): 55-71 (2004). Preclinical evidence demonstrates that sodium channel-blocking agents can suppress neuronal firing in peripheral and central sensory neurons, and it is via this mechanism that they may be useful for relieving pain. In some instances abnormal or ectopic firing can originate from injured or otherwise sensitized neurons. For example, it has been shown that sodium channels can accumulate in peripheral nerves at sites of axonal injury and may function as generators of ectopic firing (Devor et al. *J. Neurosci.*, 132: 1976 (1993)). Changes in sodium channel expression and excitability have also been shown in animal models of inflammatory pain where treatment with proinflammatory materials (CFA, Carrageenan) promoted pain-related behaviors and correlated with increased expression of sodium channel subunits (Gould et al., *Brain Res.*, 824(2): 296-9 (1999); Black et al., *Pain*, 108(3): 237-47 (2004)). Alterations in either the level of expression or distribution of sodium channels, therefore, may have a major influence on neuronal excitability and pain-related behaviors.

Many patients with either acute or chronic pain disorders respond poorly to current pain therapies and resistance or insensitivity to opiates is common. In addition, many of the currently available treatments have undesirable side effects. It has been reported that there is no treatment to prevent the development of neuropathic pain or to control established neuropathic pain. Mannion et al., *Lancet*, 353: 1959-1964 (1999).

Ohkawa et al. have described a class of cyclic ethers that are of use as sodium channel blockers (U.S. Pat. No. 6,172,085).

Currently, gabapentin is the principal treatment for neuropathic pain. As with epilepsy, its mechanism of action for pain is unknown. However, as little as only 30% of patients respond to gabapentin treatment for neuropathic pain.

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

It has now been discovered that various substituted aryl sulfonamides are potent modulators of sodium channels. In the discussion that follows, the invention is exemplified by reference to the inhibition of sodium channels that are localized in the peripheral nervous system, and in particular those compounds that are selective inhibitors of TTX-s sodium channels, and are useful for treating pain through the inhibition of sodium ion flux through channels that include a TTX-s sodium channel subunit. The compounds, compositions and methods of the present invention are useful for treating diseases in which modulating one or more TTX-s sodium channels provides relief from the disease. Of particular interest is the use of the compounds, compositions and methods of the invention for treating pain and central or peripheral nervous system disorders, preferably peripheral nervous system disorders. The present invention is of use for treating acute, chronic, inflammatory, and/or neuropathic pain.

The present invention provides compounds that are useful in the treatment of diseases through the modulation of sodium ion flux through voltage-dependent sodium channels. More particularly, the invention provides compounds, compositions and methods that are useful in ameliorating or alleviating conditions susceptible to such ion channel modulation as more fully described below.

In a first aspect, the invention provides a compound according to Formula I:

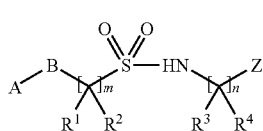

In this formula, $R^1$, $R^2$, $R^3$ and $R^4$ are independently selected from H, F, $CF_3$, substituted or unsubstituted $C_1$-$C_4$ alkyl, unsubstituted 4- to 7-membered cycloalkyl and unsubstituted 4- to 7-membered heterocycloalkyl.

The symbol A represents a member selected from:

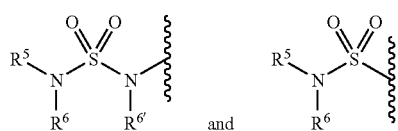

$R^5$ is selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^6$ and $R^{6'}$ are independently selected from H, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^5$ and $R^6$ are optionally joined to form a member selected from a substituted or unsubstituted cycloalkyl moiety or a substituted or unsubstituted heterocycloalkyl moiety.

The symbol B represents a member selected from:

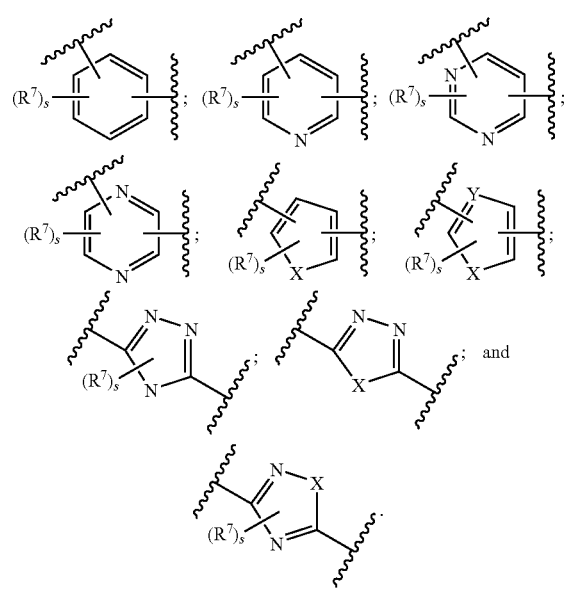

The symbol X represents a member selected from O and S.
The symbol Y represents a member selected from CH and N. The index s represents an integer greater than 0, sufficient to satisfy the valence requirements of the ring atoms. Each $R^7$ is independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ is selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^9$ and $R^{10}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, s is 1 and $R^7$ is a member selected from chloro and fluoro. In an exemplary embodiment, s is 2 and each $R^7$ is a member independently selected from chloro and fluoro. In an exemplary embodiment, s is 2 and each $R^7$ is fluoro. In an exemplary embodiment, B is a member selected from

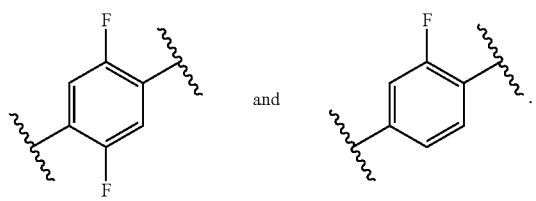

The symbol Z is a member selected from:

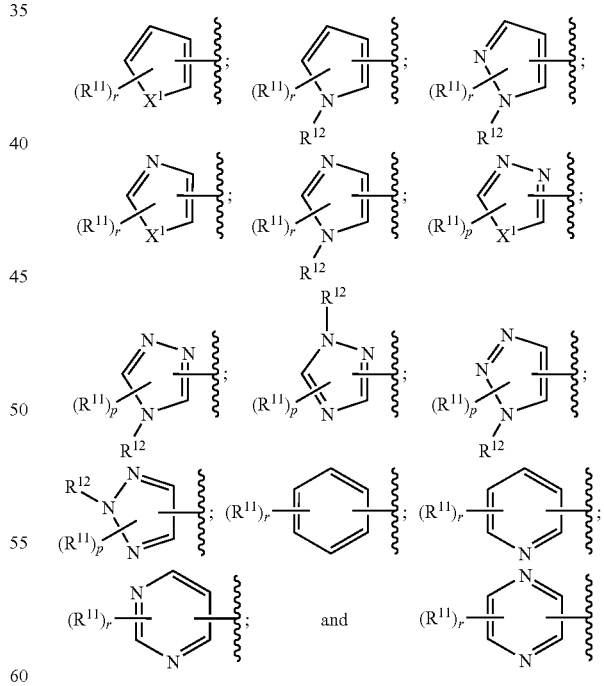

Each $R^{11}$ is a member independently selected from H, $OR^{13}$, $NR^{14}$, $R^{15}$, $SO_2NR^{14}$, $R^{15}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{13}$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$, together with the nitrogen to which they are bound, can be optionally joined to form a substituted or unsubstituted 5- to 7-membered ring. The index r represents a member selected from the integers from 0 to 2. The index p represents a member selected from the integers from 0 to 1. $R^{12}$ is selected from H, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The indices m and n independently represent an integer selected from 0 to 2, such that when a member selected from m and n can be greater than 1, each $R^1$ and $R^2$; $R^3$ and $R^4$, respectively, can be independently selected.

In another aspect, the present invention provides pharmaceutical compositions comprising a pharmaceutically acceptable excipient and a compound as provided above.

In yet another aspect, the present invention provides a method for modulating the activity of a sodium channel in a subject, comprising administering to a subject an amount of a compound as provided above which is sufficient to modulate the activity.

In still another aspect, the present invention provides a method of ameliorating or alleviating a condition in a subject. The condition can be a member selected from, among others, pain, irritable bowel syndrome, Crohn's disease, epilepsy, seizures multiple sclerosis, bipolar depression and tachyarrhythmias. The method comprises administering to the subject an amount of a compound of the invention sufficient to ameliorate or alleviate said condition.

Additional aspects, advantages and objects of the present invention will be apparent from the detailed description that follows.

DETAILED DESCRIPTION OF THE INVENTION

Abbreviations

The abbreviations used herein generally have their conventional meaning within the chemical and biological arts. For example: CHO, Chinese hamster ovary; EBSS, Earl's Balanced Salt Solution; SDS, sodium dodecyl sulfate; $Et_3N$, triethylamine; MeOH, methanol; and DMSO, dimethylsulfoxide.

Definitions

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Acute pain", as described above, refers to pain which is marked by short duration or a sudden onset.

"Chronic pain", as described above, refers to pain which is marked by long duration or frequent recurrence.

"Inflammatory pain", as described above, refers to pain which is produced as a symptom or a result of inflammation or an immune system disorder.

"Visceral pain", as described above, refers to pain which is located in an internal organ.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to the compounds discussed herein, pharmaceutically acceptable salts and prodrugs of these compounds.

"Inhibiting" and "blocking," are used interchangeably herein to refer to the partial or full blockade of a voltage sodium gated channel by a compound of the invention, which leads to a decrease in ion flux either into or out of a cell in which a voltage-gated sodium channel is found.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N) and sulfur (S).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

DESCRIPTION OF THE EMBODIMENTS

I. The Compounds

In a first aspect, the invention provides a compound according to Formula I:

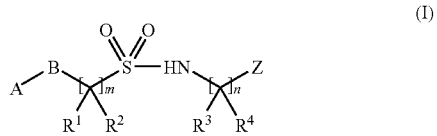

(I)

In this formula, R$^1$, R$^2$, R$^3$ and R$^4$ are members independently selected from H, F, CF$_3$, substituted or unsubstituted C$_1$-C$_4$ alkyl, unsubstituted 4- to 7-membered cycloalkyl and unsubstituted 4- to 7-membered heterocycloalkyl.

The symbol A represents a member selected from:

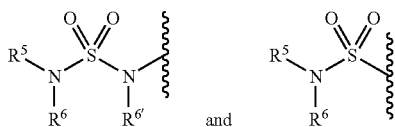

$R^5$ is a member selected from OR*, NR*R**, SR*, —S(O)R*, —S(O)$_2$R*, —S(O)$_2$NR*R**, —C(O)R*, —C(O)OR*, —C(O)NR*R**, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Each R* and R** is a member independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The index q represents a member selected from the integers from 0 to 2. $R^6$ and $R^{6'}$ are independently selected from H, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^5$ and $R^6$ are optionally joined to form a member selected from substituted or unsubstituted cycloalkyl or substituted or unsubstituted heterocycloalkyl.

The symbol B represents a member selected from:

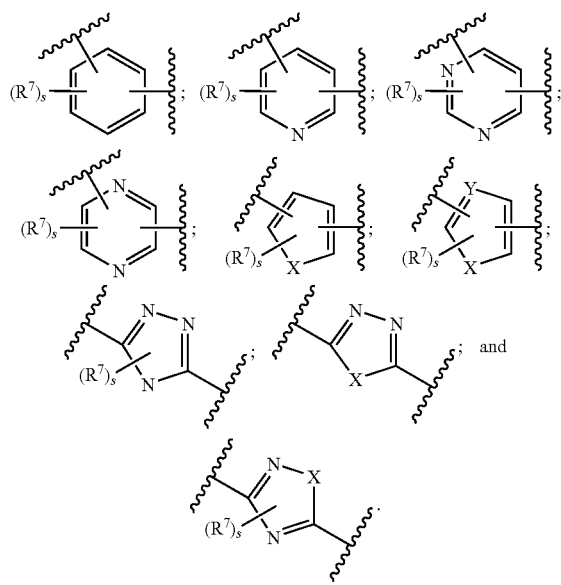

The symbol X represents a member selected from O and S.

The symbol Y represents a member selected from CH and N. The index s represents an integer greater than 0, sufficient to satisfy the valence requirements of the ring atoms. Each $R^7$ is independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ is selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^9$ and $R^{10}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The symbol Z is selected from:

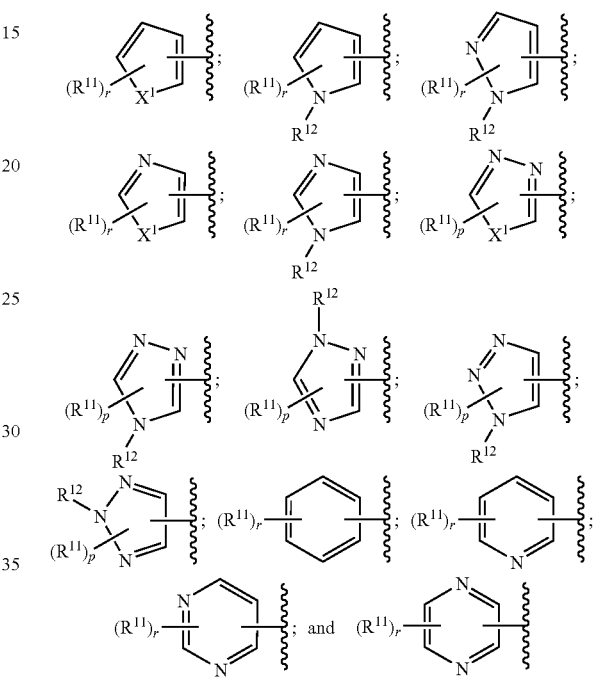

Each $R^{11}$ is selected from H, $OR^{13}$, $NR^{14}R^{15}$, $SO_2NR^{14}R^{15}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{13}$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{14}$ and $R^{15}$, together with the nitrogen to which they can be bound, can be optionally joined to form a substituted or unsubstituted 5- to 7-membered ring. The index r represents a member selected from the integers from 0 to 2. The index p represents a member selected from the integers from 0 to 1. $R^{12}$ is a member selected from $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. The indices m and n can independently represent an integer selected from 0 to 2, such that when a member selected from m and n can be greater than 1, each $R^1$ and $R^2$; $R^3$ and $R^4$, respectively, can be independently selected. $X^1$ is S.

In an exemplary embodiment, the indices m and n can be 0. In another exemplary embodiment, the symbol A is a member selected from

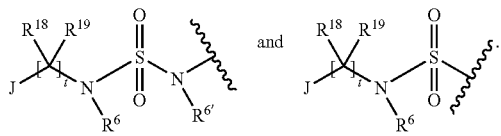

J is a member selected from OR*, NR*R**, SR*, —S(O)R*, —S(O)$_2$R*, —S(O)$_2$NR*R**, —C(O)R*, —C(O)OR*, —C(O)NR*R**, $C_1$-$C_4$ substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Each R* and R** is a member independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{18}$ and $R^{19}$ are members independently selected from H, substituted or unsubstituted alkyl, substituted or unsubstituted heteroalkyl, and substituted or unsubstituted aryl. $R^{18}$ and $R^{19}$, together with each carbon to which each of $R^{18}$ and $R^{19}$ are attached, are optionally joined to form a member selected from substituted or unsubstituted 3- to 7-member cycloalkyl moiety and substituted or unsubstituted 5- to 7-member heterocycloalkyl moiety. The index t is an integer selected from 0 to 4, such that when t is greater than 1, each $R^{18}$ and $R^{19}$ is independently selected. $R^6$ and $R^{18}$, together with the atoms to which $R^6$ and $R^{18}$ are attached, are optionally joined to form a substituted or unsubstituted 4- to 7-member heterocycloalkyl moiety. $R^6$ and J, together with the atoms to which $R^6$ and J are attached, are optionally joined to form a member selected from substituted or unsubstituted 3- to 7-member cycloalkyl moiety and substituted or unsubstituted 5- to 7-member heterocycloalkyl moiety.

In an exemplary embodiment, J is a member selected from substituted or unsubstituted alkyl, substituted or unsubstituted cycloalkyl, substituted or unsubstituted cycloalkyloxy, substituted or unsubstituted cycloalkylthio, substituted or unsubstituted cycloalkylamino, substituted or unsubstituted heteroalkyl, substituted or unsubstituted heterocycloalkyl, substituted or unsubstituted heterocycloalkyloxy, substituted or unsubstituted heterocycloalkylthio, substituted or unsubstituted heterocycloalkylamino, substituted or unsubstituted aryl, substituted or unsubstituted aryloxy, substituted or unsubstituted arylthio, substituted or unsubstituted arylamino, substituted or unsubstituted heteroaryl, substituted or unsubstituted heteroaryloxy, substituted or unsubstituted heteroarylthio, and substituted or unsubstituted heteroarylamino.

In an exemplary embodiment, J is substituted or unsubstituted aryl. In an exemplary embodiment, J is substituted or unsubstituted phenyl. In an exemplary embodiment, a substituent on the substituted phenyl is a member selected from halogen, methyl, trifluoromethyl, ethyl, t-butyl, methoxy and chlorothienyl. In another exemplary embodiment, substituted phenyl is a member selected from chlorophenyl, fluorophenyl, dichlorophenyl, difluorophenyl, chlorofluorophenyl, trifluoromethylfluorophenyl, trifluoromethylchlorophenyl, t-butylchlorophenyl, t-butylfluorophenyl, methylchlorophenyl, methylfluorophenyl, methoxychlorophenyl, and methoxyfluorophenyl.

In an exemplary embodiment, J is substituted or unsubstituted aryloxy. In an exemplary embodiment, J is substituted or unsubstituted phenoxy. In an exemplary embodiment, a substituent on the substituted phenoxy is a member selected from halogen, methyl, trifluoromethyl, ethyl, t-butyl, methoxy and chlorothienyl. In another exemplary embodiment, substituted phenoxy is a member selected from chlorophenoxy, fluorophenoxy, dichlorophenoxy, difluorophenoxy, chlorofluorophenoxy, trifluoromethylfluorophenoxy, trifluoromethylchlorophenoxy, t-butylchlorophenoxy, t-butylfluorophenoxy, methylchlorophenoxy, methylfluorophenoxy, methoxychlorophenoxy, and methoxyfluorophenoxy.

In an exemplary embodiment, J is substituted or unsubstituted phenylamino. In an exemplary embodiment, a substituent on the substituted phenylamino is a member selected from halogen, methyl, trifluoromethyl, ethyl, t-butyl, methoxy and chlorothienyl. In another exemplary embodiment, substituted phenylamino is a member selected from chlorophenylamino, fluorophenylamino, dichlorophenylamino, difluorophenylamino, chlorofluorophenylamino, trifluoromethylfluorophenylamino, trifluoromethylchlorophenylamino, t-butylchlorophenylamino, t-butylfluorophenylamino, methylchlorophenylamino, methylfluorophenylamino, methoxychlorophenylamino, and methoxyfluorophenylamino.

In an exemplary embodiment, J is substituted or unsubstituted pyridinyloxy. In an exemplary embodiment, J is unsubstituted pyridinyloxy. In an exemplary embodiment, a substituent on the substituted pyridinyloxy is a member selected from halogen, methyl, trifluoromethyl, ethyl, t-butyl, methoxy and chlorothienyl. In another exemplary embodiment, substituted pyridinyloxy is a member selected from chloropyridinyloxy, fluoropyridinyloxy, dichloropyridinyloxy, difluoropyridinyloxy, chlorofluoropyridinyloxy, trifluoromethylfluoro pyridinyloxy, trifluoromethylchloropyridinyloxy, t-butylchloropyridinyloxy, t-butylfluoropyridinyloxy, methylchloropyridinyloxy, methylfluoropyridinyloxy, methoxychloropyridinyloxy, and methoxyfluoropyridinyloxy.

In an exemplary embodiment, J is substituted or unsubstituted benzo[1,4]dioxin-2-yl. In an exemplary embodiment, J is unsubstituted benzo[1,4]dioxin-2-yl. In an exemplary embodiment, a substituent on the substituted benzo[1,4]dioxin-2-yl is a member selected from halogen, methyl, trifluoromethyl, ethyl, t-butyl, methoxy and chlorothienyl. In another exemplary embodiment, substituted benzo[1,4]dioxin-2-yl is a member selected from chlorobenzo[1,4]dioxin-2-yl, fluorobenzo[1,4]dioxin-2-yl, dichlorobenzo[1,4]dioxin-2-yl, difluorobenzo[1,4]dioxin-2-yl, chlorofluorobenzo[1,4]dioxin-2-yl, trifluoromethylfluorobenzo[1,4]dioxin-2-yl, trifluoromethylchlorobenzo[1,4]dioxin-2-yl, t-butylchlorobenzo [1,4]dioxin-2-yl, t-butylfluorobenzo[1,4]dioxin-2-yl, methylchlorobenzo[1,4]dioxin-2-yl, methylfluorobenzo[1,4]dioxin-2-yl, methoxychlorobenzo[1,4]dioxin-2-yl, and methoxyfluorobenzo[1,4]dioxin-2-yl.

In an exemplary embodiment, J is substituted or unsubstituted alkyl. In an exemplary embodiment, J is a member selected from methyl, ethyl, propyl, and 3,3 dimethylbutyl. In an exemplary embodiment, a substituent on the substituted alkyl is a member selected from halogen, methyl, trifluoromethyl, ethyl, t-butyl, methoxy, and chlorothienyl.

In an exemplary embodiment, J is a member selected from

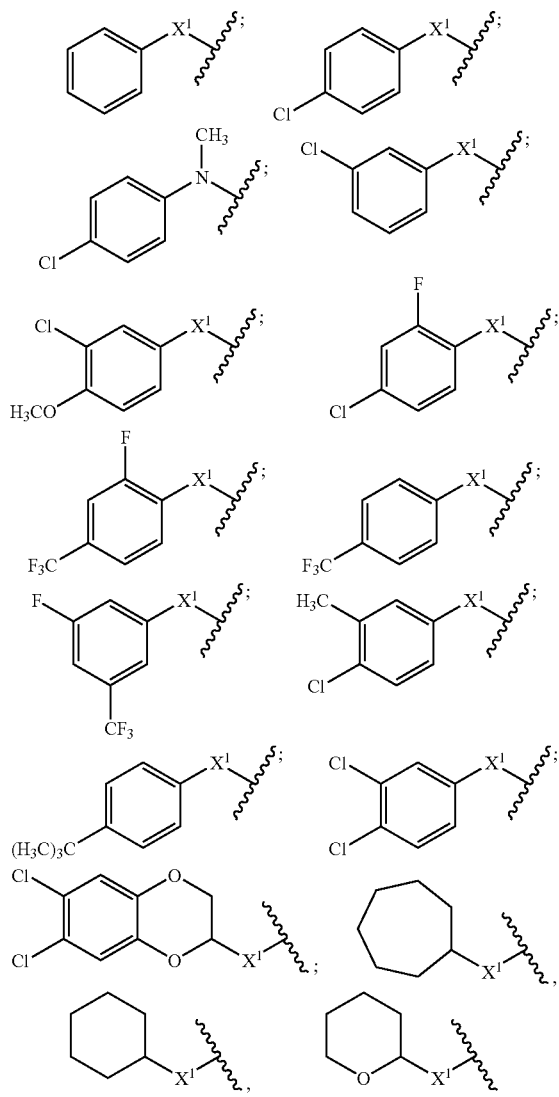

wherein $X^1$ is a member selected O, S, —NH—, —N(CH$_3$)—, and a bond.

In an exemplary embodiment, t is 1, $R^{18}$ is H and $R^{19}$ is H. In an exemplary embodiment, t is 1, $R^{18}$ is CH$_3$ and $R^{19}$ is H. In an exemplary embodiment, t is 1, $R^{18}$ is CH$_3$ and $R^{19}$ is CH$_3$. In an exemplary embodiment, t is 1, $R^{18}$ and $R^{19}$, along with the atom to which they are attached, are joined to form a member selected from a cyclopropyl, cyclobutyl, cyclopentyl and cyclohexyl ring. In an exemplary embodiment, t is 1, $R^{18}$ and $R^{19}$, along with the atom to which they are attached, are joined to form a cyclobutyl ring.

In an exemplary embodiment, t is 2, and each $R^{18}$ is H and each $R^{19}$ is H. In an exemplary embodiment, t is 2, and at least one $R^{18}$ is CH$_3$ and at least one $R^{19}$ is H. In an exemplary embodiment, t is 2, and at least one $R^{18}$ is CH$_3$ and at least one $R^{19}$ is CH$_3$. In an exemplary embodiment, t is 2, $R^{18}$ and $R^{19}$, along with the atom to which they are attached, are joined to form a member selected from a cyclopropyl, cyclobutyl, cyclopentyl and cyclohexyl ring. In an exemplary embodi- ment, t is 2, $R^{18}$ and $R^{19}$, along with the atom to which they are attached, are joined to form a cyclobutyl ring.

In an exemplary embodiment, $R^6$ and $R^{18}$, together with the atoms to which $R^6$ and $R^{18}$ are attached, are joined to form a member selected from a substituted or unsubstituted azetidi- nyl, pyrrolidinyl, piperazinyl, or piperidinyl moiety. In an exemplary embodiment, $R^6$ and $R^{18}$, together with the atoms to which $R^6$ and $R^{18}$ are attached, are joined to form an unsubstituted azetidinyl moiety. In an exemplary embodi- ment, $R^6$ and $R^{18}$, together with the atoms to which $R^6$ and $R^{18}$ are attached, are joined to form an unsubstituted piperidi- nyl moiety.

In an exemplary embodiment, $R^8$ and J, together with the atoms to which $R^6$ and J are attached, are joined to form a member selected from substituted or unsubstituted 3- to 7-member cycloalkyl moiety and substituted or unsubstituted 5- to 7-member heterocycloalkyl moiety. In an exemplary embodiment, $R^6$ and J, together with the atoms to which $R^6$ and J are attached, are joined to form a member selected from a substituted or unsubstituted azetidinyl, pyrrolidinyl, piper- azinyl, or piperidinyl moiety.

In another exemplary embodiment, the symbol A is a mem- ber selected from

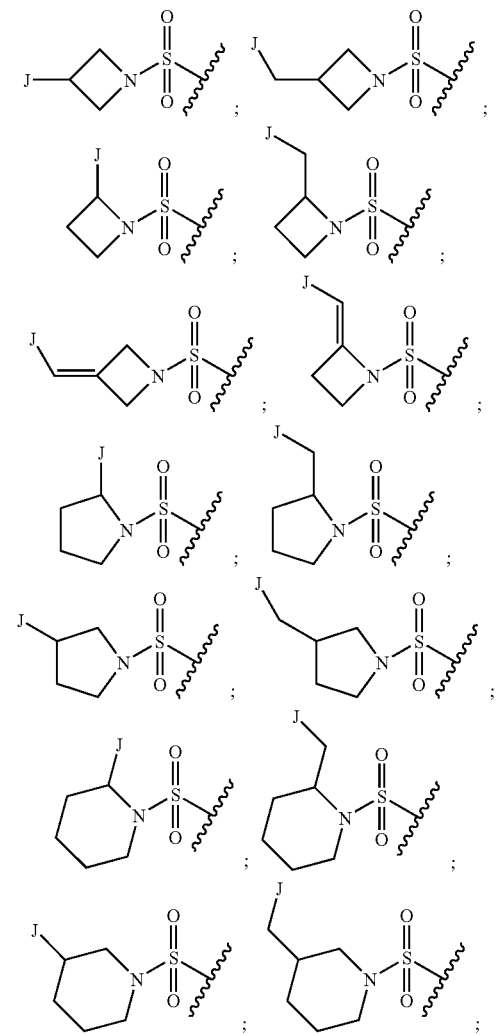

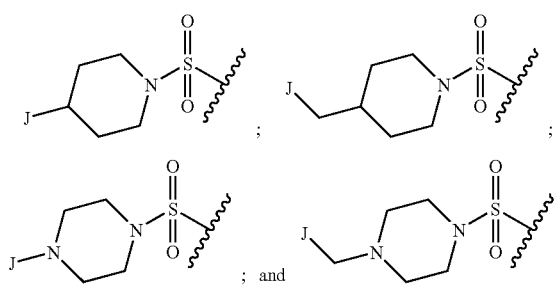

In another exemplary embodiment, the symbol A is a member selected from

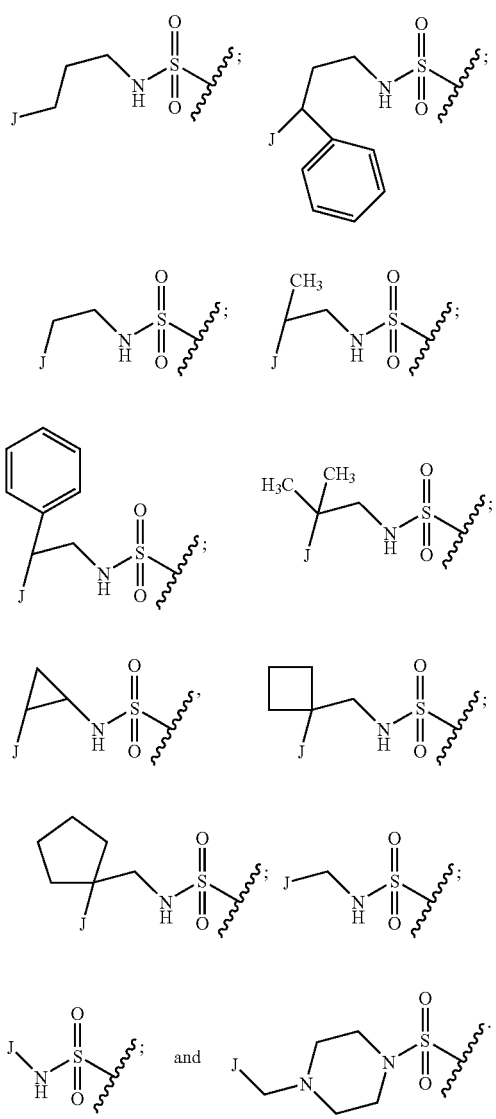

In an exemplary embodiment, $R^6$ is $CH_3$.

In another exemplary embodiment, the compound has a structure according to Formulae (II), (IIa), (III) or (IIIa):

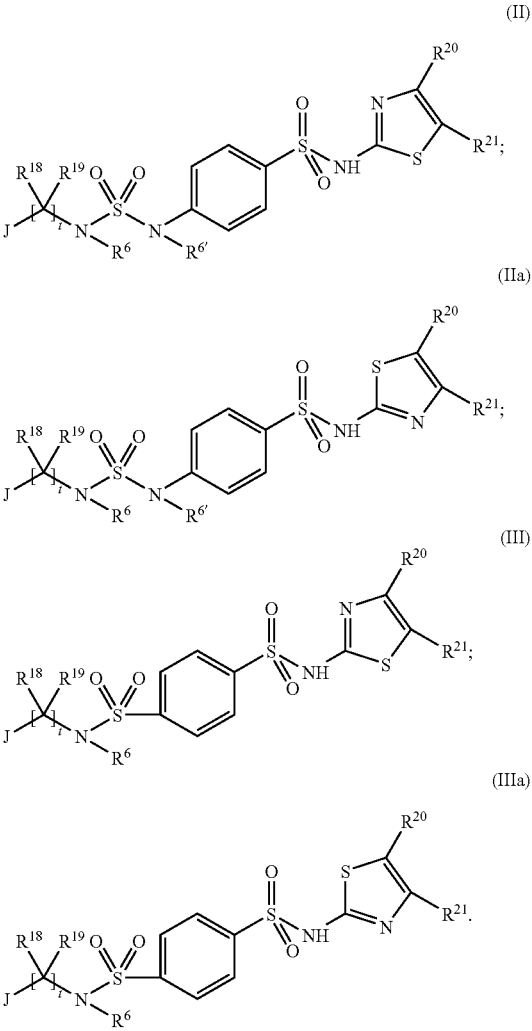

$R^{20}$ and $R^{21}$ are members independently selected from H, $OR^{22}$, $NR^{23}R^{24}$, $SO_2NR^{23}R^{24}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{22}$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{23}$ and $R^{24}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In an exemplary embodiment, $R^{20}$ is H and $R^{21}$ is halogen. In an exemplary embodiment, $R^{20}$ is halogen and $R^{21}$ is H. In an exemplary embodiment, $R^{20}$ is H and $R^{21}$ is Cl. In an exemplary embodiment, $R^{20}$ is Cl and $R^{21}$ is H. In an exemplary embodiment, $R^{20}$ is H and $R^{21}$ is F. In an exemplary embodiment, $R^{20}$ is F and $R^{21}$ is H. In an exemplary embodiment, $R^{20}$ is Cl and $R^{21}$ is F. In an exemplary embodiment, $R^{20}$ is F and $R^{21}$ is F. In an exemplary embodiment, $R^{20}$ is Cl and $R^{21}$ is Cl.

In another exemplary embodiment, the compound has a structure according to Formulae (II), (IIa), (III) or (IIIa) wherein the combination of $R^{20}$ and $R^{21}$ are as described in paragraph 88 and wherein J is a member selected from a species described in paragraph 71, 72, 73, 74, 75, 76, 77, 78 or 79.

In a further exemplary embodiment, the compound has the formula:

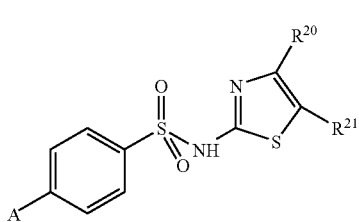

(IV)

wherein $R^{20}$ and $R^{21}$ are as described above.

In a further exemplary embodiment, the compound has a formula which is a member selected from:

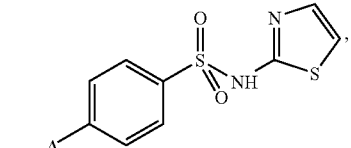

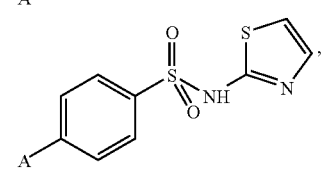

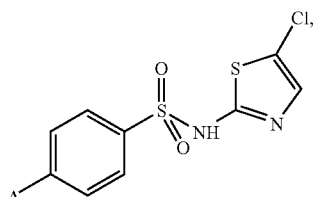

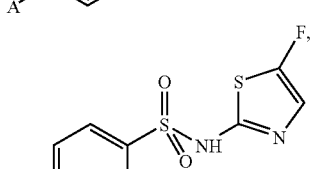

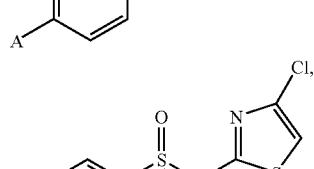

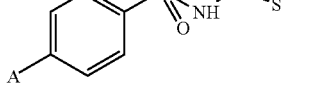

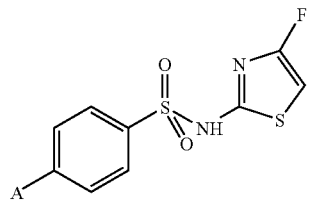

wherein the symbol A is a member selected from

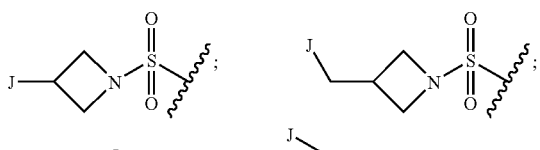

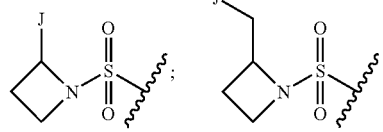

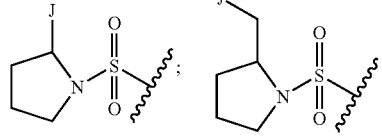

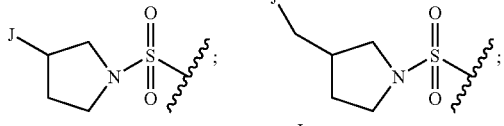

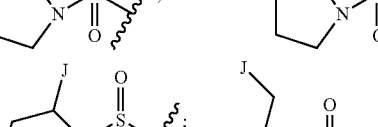

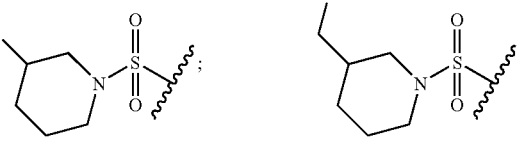

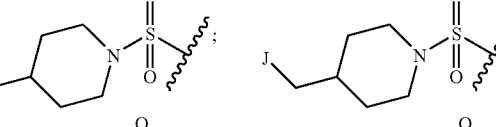

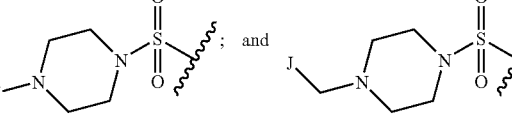

In a further exemplary embodiment, the compound has a formula which is a member selected from:

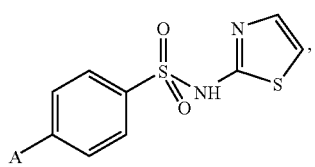

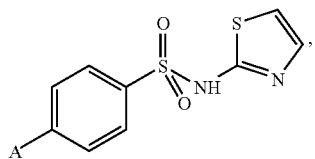

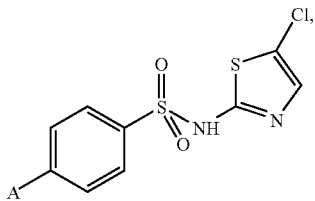

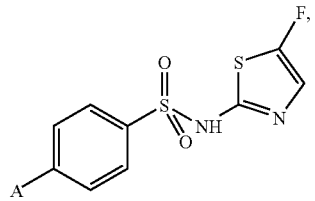

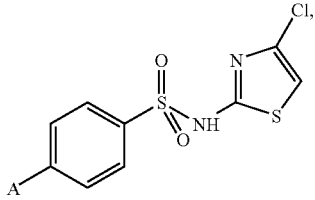

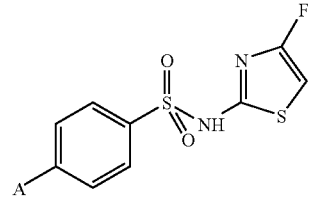

wherein the symbol A is a member selected from

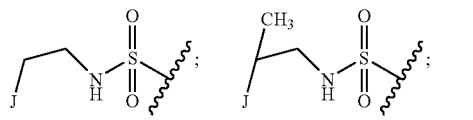

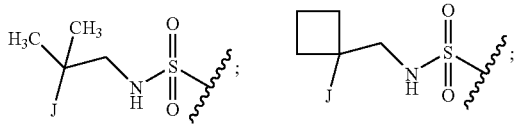

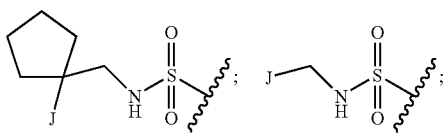

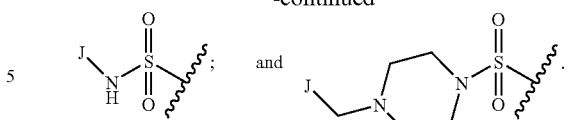

In another exemplary embodiment, B is a member selected from:

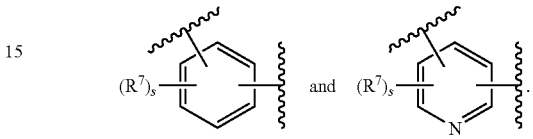

The index s is an integer greater than 0, sufficient to satisfy the valence requirements of the ring atoms. Each $R^7$ is a member independently selected from H, $OR^8$, $NR^9R^{10}$, $SO_2NR^9R^{10}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^9$ and $R^{10}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In another embodiment, the compound has a formula selected from:

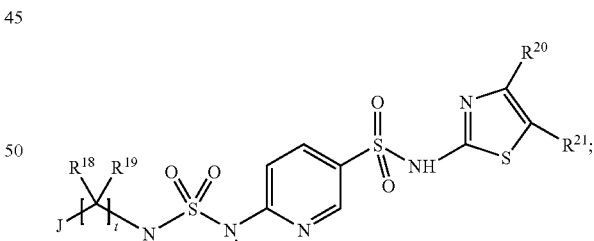

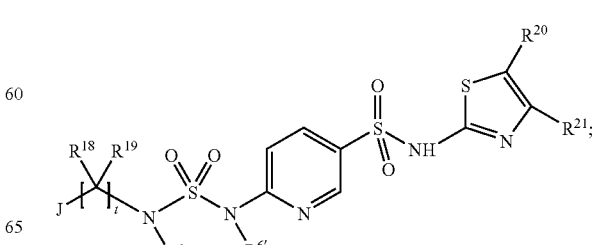

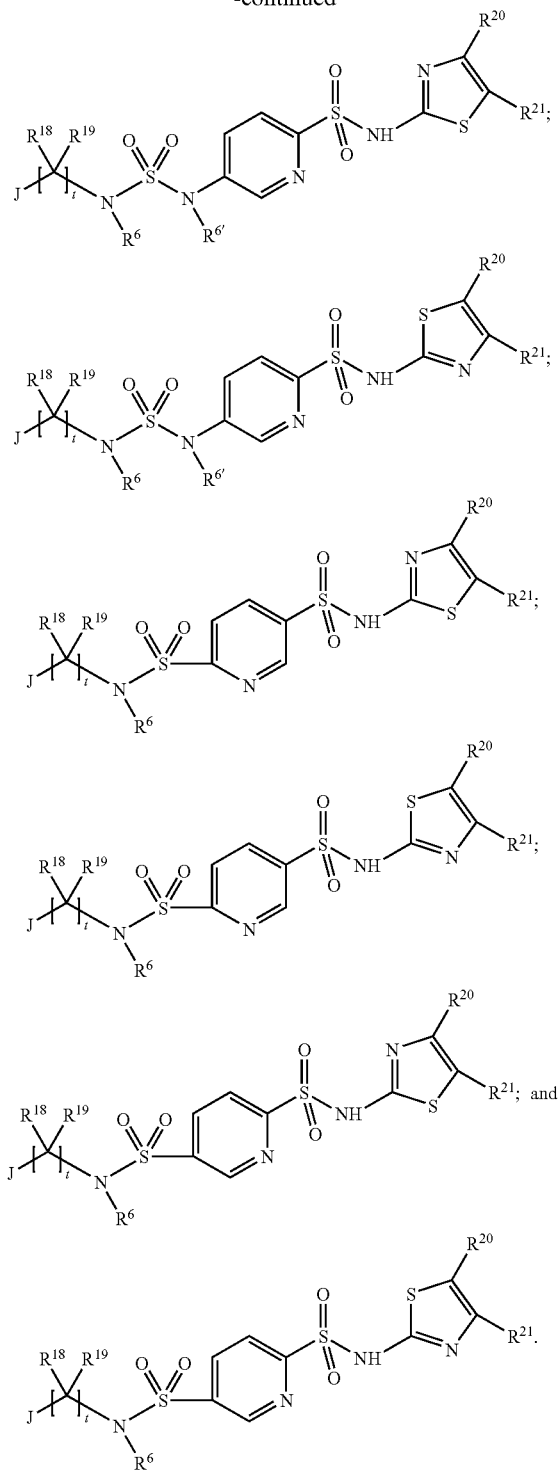

J is a member selected from substituted or unsubstituted alkyl, substituted or unsubstituted cycloalkyl, substituted or unsubstituted heteroalkyl, substituted or unsubstituted heterocycloalkyl, substituted or unsubstituted aryl and substituted or unsubstituted heteroaryl. $R^{18}$ and $R^{19}$ are members independently selected from H, substituted or unsubstituted alkyl, substituted or unsubstituted heteroalkyl, and substituted or unsubstituted aryl. $R^{18}$ and $R^{19}$, together with each carbon to which each of $R^{18}$ and $R^{19}$ are attached, are optionally joined to form a member selected from a substituted or unsubstituted 3- to 7-member cycloalkyl moiety and substituted or unsubstituted 5- to 7-member heterocycloalkyl moiety. The index t is an integer selected from 0 to 4, such that when t is greater than 1, each $R^{18}$ and $R^{19}$ is independently selected. $R^{20}$ and $R^{21}$ are members independently selected from H, $OR^{22}$, $NR^{23}R^{24}$, $SO_2NR^{23}R^{24}$, cyano, halogen, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{22}$ is a member selected from H, $CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{23}$ and $R^{24}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{23}$ and $R^{24}$, together with the nitrogen to which they are bound, are optionally joined to form a substituted or unsubstituted 5- to 7-membered ring.

In an exemplary embodiment, J is a member selected from substituted or unsubstituted alkyl, substituted or unsubstituted cycloalkyl, substituted or unsubstituted cycloalkyloxy, substituted or unsubstituted cycloalkylthio, substituted or unsubstituted cycloalkylamino, substituted or unsubstituted heteroalkyl, substituted or unsubstituted heterocycloalkyl, substituted or unsubstituted heterocycloalkyloxy, substituted or unsubstituted heterocycloalkylthio, substituted or unsubstituted heterocycloalkylamino, substituted or unsubstituted aryl, substituted or unsubstituted aryloxy, substituted or unsubstituted arylthio, substituted or unsubstituted arylamino, substituted or unsubstituted heteroaryl, substituted or unsubstituted heteroaryloxy, substituted or unsubstituted heteroarylthio, and substituted or unsubstituted heteroarylamino.

Representative compounds of the invention are set forth in Table II. In an exemplary embodiment, the compound is a compound set forth in Table II.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, can be attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within a motif described herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. *Polymeric Drugs and Drug Delivery Systems*, ACS Symposium Series Vol. 469, American Chemical Society, Washington, D.C. 1991.

In a second aspect, the invention provides a pharmaceutical formulation comprising a compound according a formula described herein. In an exemplary embodiment, the invention provides a pharmaceutical formulation comprising a compound described herein. In an exemplary embodiment, the invention provides a pharmaceutical formulation comprising a compound according to Formula I.

In a third aspect, the invention provides a method of modulating the activity of a sodium channel in a subject. This method comprises administering to a subject an amount of a compound according a formula described herein sufficient to modulate said activity. In an exemplary embodiment, the method comprises administering to a subject an amount of a compound described herein sufficient to modulate said activity. This method comprises administering to a subject an amount of a compound according a formula described herein sufficient to modulate said activity. In an exemplary embodiment, the method comprises administering to a subject an amount of a compound according to Formula I sufficient to modulate said activity. Methods of detecting and amplifying modulation of a sodium channel are generally known in the art. A representative method is set forth in Section III, herein.

In a fourth aspect, the invention provides a method of ameliorating or alleviating a condition in a subject. The condition can be a member selected from pain, irritable bowel syndrome, Crohn's disease, epilepsy, seizures multiple sclerosis, bipolar depression and tachy-arrhythmias. The method includes administering to the subject an amount of the compound described herein sufficient to ameliorate or alleviate the condition. In an exemplary embodiment, the condition is pain, and the pain can be a member selected from acute pain, chronic pain, visceral pain, inflammatory pain and neuropathic pain. Exemplary aspects of this method are described in greater detail in section VI, herein.

II. Preparation of the Compounds

Compounds of the present invention can be prepared using readily available starting materials or known intermediates. The synthetic schemes set forth below provide exemplary synthetic pathways for the preparation of compounds of the invention.

II. a. General Procedure for Synthesizing Sulfamide-containing Compounds i)

Sulfamide-containing compounds of the invention can be synthesized as shown in Scheme A.

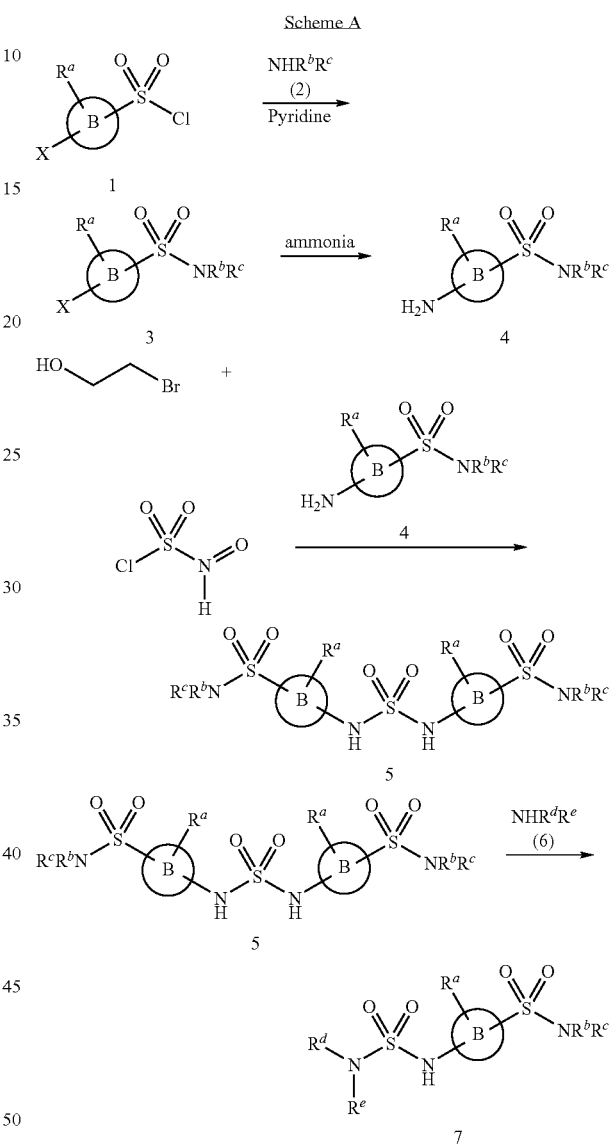

In this scheme, 1 is reacted with 2 in pyridine, forming 3. Compound 3 is next reacted with an amine-containing species such as ammonia in order to produce substituted amino aryl sulfonamide 4. In some instances compound 4 can also be purchased from commercial sources or prepared from commercially available starting materials, such as aryl amines.

Compound 5 was synthesized by reacting 4 with 2-bromoethanol and chlorosulfonyl isocyanate. Compound 7 was formed by the reaction of an appropriately substituted amine 6 with substituted amino aryl sulfonamide 5 in an organic solvent, such as acetonitrile, in the presence of pyridine or triethylamine at an elevated temperature, e.g., 90° C.

ii.)

The synthesis of compounds of general formulae 7 can also be achieved as outlined in Scheme B.

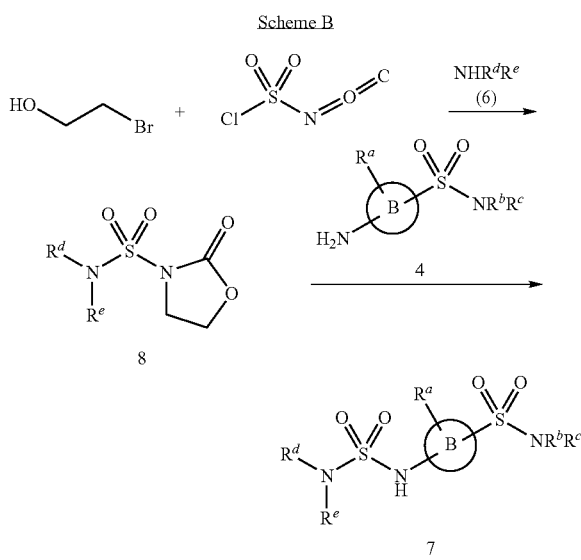

Oxazolidinone 8 was synthesized by reacting amine 6 with the product of the reaction of 2-bromoethanol and chlorosulfonyl isocyanate in the presence of a base such as triethylamine. The reaction of the oxazolidinone 8 with 4 provides 7.

II.c. General Procedure for Synthesizing Sulfonamide-containing Compounds

Sulfonamide-containing compounds of the invention can be synthesized as shown in scheme C.

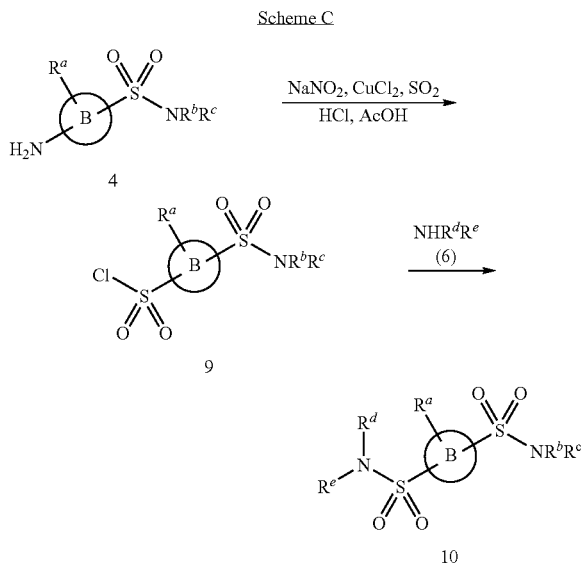

A typical procedure for the synthesis of 10 involved the reaction of a sulfonyl chloride 9 with an amine 6 in the presence of a base such as triethyl amine. The sulfonyl chloride 9 was prepared by reacting a substituted aryl amine 4 with $NaNO_2$ in the presence of $CuCl_2$ followed by reaction with sulfur dioxide.

III. Assays for Blockers of Voltage-Dependent TTX-Sensitive Sodium Channels

The activity of sodium channels can be assessed using a variety of in vitro assays, including but not limited to, measuring ion flux, measuring transmembrane potential, and/or measuring ionic current. Measurement of ionic fluxes can be accomplished by measuring changes in the concentration of the permeant species or by tracking the movement of small amounts of an appropriately permeant radioactive tracer. Transmembrane potential can be assessed with voltage-sensitive fluorescent dyes or, more sensitively, with electrophysiological methods.

Determination of the effectiveness of compounds as ex vivo blockers of sodium channels can be assessed by the inhibition of compound action potential propagation in isolated nerve preparations (Kourtney and Stricharz, LOCAL ANESTHETICS, Springer-Verlag, New York, 1987). A number of experimental models in the rat are appropriate for assessing the in vivo efficacy of the compounds of the invention. For example, the neuropathic pain model produced by the tight ligation of spinal nerves, described by Kim et al., Pain, 50: 355-363 (1992), can be used to experimentally determine the effect of the compounds of the invention in an in vivo model of pain. Mechanical sensitivity can also be assessed using a procedure described by Chaplan et al., J. Neurosci. Methods, 53: 55-63 (1994). Other assays of use are known to those of skill in the art.

Modulators of TTX-sensitive sodium channels can be tested using biologically active recombinant channels, or naturally occurring TTX-sensitive sodium channels, or by using native cells, like neurons expressing a TTX-sensitive sodium current. TTX-sensitive sodium channels can be isolated, co-expressed or expressed in a cell, or expressed in a membrane derived from a cell. In such assays, TTX-sensitive sodium channels are generally expressed alone to form a homomeric sodium channel or may be co-expressed with a second subunit (e.g., an auxiliary beta subunit) so as to form a heteromeric sodium channel. The TTX-sensitive sodium channels are stably expressed in HEK-293 cells, an example of an effective mammalian expression system.

Modulation can be tested using one of the in vitro or in vivo assays described above. Samples or assays that are treated with a potential sodium channel inhibitor are compared to control samples without the test compound, to examine the extent of modulation. Control samples (untreated with inhibitors) are assigned a relative sodium channel activity value of 100. Inhibition of TTX-sensitive sodium channels is achieved when the sodium channel activity value relative to the control is less than 70%, preferably less than 40% and still more preferably, less than 30%. Compounds that decrease the flux of ions will cause a detectable decrease in the ion current density by decreasing the probability of a TTX-sensitive sodium channel being open, by decreasing conductance through the channel, decreasing the number of channels, or decreasing the expression of channels.

Changes in ion flux may be asssesed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated patch" mode, the "whole cell" mode or other means of controlling or measuring changes in transmembrane potential (see, e.g., Ackerman et al., New Engl. J. Med., 336: 1575-1595 (1997)). Whole cell currents are conveniently determined using the standard methodology (see, e.g., Hamill et al., *Pflugers. Archiv.* 391: 85 (1981). Other known assays include: radiotracer flux assays and fluorescence assays using voltage-sensitive dyes (see, e.g., Vestergarrd-Bogind et al., *J. Membrane Biol.* 88: 67-75 (1988); Daniel et al., *J. Pharmacol. Meth.* 25: 185-193 (1991); Holevinsky et al, *J. Membrane Biology* 137: 59-70 (1994)). Assays for compounds capable of inhibiting or increasing sodium flux through the channel proteins can be performed by application of the compounds to a bath solution in contact with and comprising cells having a channel of the present invention (see, e.g., Blatz et al., *Nature* 323: 718-720 (1986); Park, *J. Physiol.* 481: 555-570 (1994)). Generally, the compounds to be tested are present in the range from about 1 nM to about 100 mM, preferably from about 1 nM to about 30 µM. In an exemplary embodiment, the compounds to be tested are present in the range from about 1 nM to about 3 µM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see U.S. Pat. No. 5,688,830). The cations can be measured in a variety of standard ways. They can be measured directly by concentration changes of the ions or indirectly by membrane potential or by using radioactive ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidate compounds of the invention. Physiologically, sodium channels open and close on a millisecond timescale. To overcome the short time in which channels are open the HTS assay can be run in the presence of an agent that modifies the gating of the channel, (e.g., pyrethroids, alpha-scorpion toxins, beta-scorpion toxins, batrachotoxin, etc). These agents modify the gating of sodium channels and keep the pore open for extended periods of time. In addition, while sodium channels are primarily selective for sodium, other ionic species can permeate the channel.

The specificity and effect of the TTX-sensitive sodium channel blocking agents of the invention can also be assayed against non-specific blockers of sodium channels, such as tetracaine, mexilitine, and flecainide.

IV. Pharmaceutical Compositions of VGSC Inhibitors

In another aspect, the present invention provides pharmaceutical compositions comprising a pharmaceutically acceptable excipient and a compound of the invention described herein.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound described herein, or a pharmaceutically acceptable salt of a compound described herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules.

Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Inhibiting Ion Flow in VGSC

In yet another aspect, the present invention provides methods for decreasing ion flow through voltage gated sodium channels in a cell, comprising contacting a cell containing the target ion channels with a sodium channel-inhibiting amount of a compound described herein.

The methods provided in this aspect of the invention are useful for the diagnosis of conditions that can be treated by inhibiting ion flux through voltage gated sodium channels, or for determining if a patient will be responsive to therapeutic agents, which act by inhibiting sodium channels.

VI. Methods for Treating Conditions Mediated by VGSC

In still another aspect, the present invention provides a method for the treatment of a disorder or condition through inhibition of a voltage gated sodium channel. In this method, a subject in need of such treatment is administered an effective amount of a compound described herein and/or according to a formula described herein. In a preferred embodiment, the compounds provided herein are used to treat a disorder or condition by inhibiting an ion channel of the VGSC family.

The compounds provided herein are useful as sodium channel inhibitors and find therapeutic utility via inhibition of VGSCs in the treatment of diseases or conditions. The sodium channels that are typically inhibited are described herein as VGSCs such as the $Na_v1.1$ channel.

The compounds of the invention are particularly preferred for use in the treating, preventing or ameliorating pain or seizures. The method includes administering to a patient in need of such treatment, a therapeutically effective amount of a compound described herein and/or according to a formula described herein, or a pharmaceutically acceptable salt thereof.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

Moreover, any VGSC inhibitory substance possessed of satisfactory VGSC modulating activity coupled with favorable intracranial transfer kinetics and metabolic stability is expected to show efficacy in central nervous system (CNS) diseases and disorders such as central nervous system ischemia, central nervous system trauma (e.g. brain trauma, spinal cord injury, whiplash injury, etc.), epilepsy, seizures, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine, ataxia, bipolar disorder, spasticity, mood disorders, psychotic disorders, hearing and vision loss, age-related memory loss, learning deficiencies, anxiety and cerebral edema.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLES

The following examples are offered to illustrate, but not to limit the claimed invention. In the examples below, unless otherwise stated, temperatures are given in degrees Celsius ° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or LC/MS data and yields are provided for illustration only. The following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine).

Example 1

1.1 Preparation of N-(3,4-dichloro-phenyl)-ethyl]-N'-[4-(N-thiazol-2-yl-sulfonamyl)-phenyl]-sulfamide, 7a 1.1.a Preparation of N,N'-di[4-(N-thiazol-2-yl-sulfonamyl)-phenyl]-sulfamide, 5a

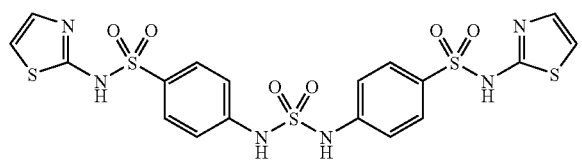

Chlorosulfonylisocyanate (3.4 mL, 39 mmol) in methylene chloride (100 mL, 2 mol) was cooled to 0° C. and then 2-bromoethanol (2.8 mL, 40 mmol) in methylene chloride (20 mL, 300 mmol) was added dropwise over 30 min. The reaction mixture was stirred for 30 min and concentrated in vacuo. To this residue was added N-(2-thiazolyl)-sulfanilamide (20.4 g, 80 mmol), 4a, in pyridine (250 mL). The reaction mixture was heated at 80° C. overnight, cooled to rt and concentrated in vacuo. To this was added 1 N HCl (100 mL) and the resulting yellow precipitate was filtered and washed with chloroform to give crude material 5a (which was used in 1.1.b without further purification). MS m/z: 573 (M+1).

1.1.b Preparation of N-(3,4-dichloro-phenyl)ethyl]-N'-[4-(N-thiazol-2-yl-sulfonamyl)-phenyl]-sulfamide, 7a

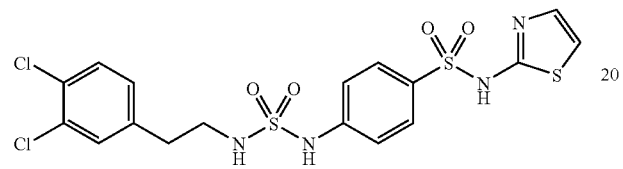

To a solution of 5a (1.0 g, 1.75 mmol) in acetonitrile, 20 mL of triethylamine (1.2 mL, 8.7 mmol) and 3,4-dichlorophenethylamine (0.285 mL, 1.92 mmol), 6a, were added. The reaction mixture was heated at 90° C. for 2 h, cooled to rt and concentrated in vacuo. The residue was partitioned between ethyl acetate and water and the organic solution was washed with 1 N HCl, brine and then dried with $MgSO_4$. The crude product was purified by column chromatography to give 125.6 mg of pure product 7a, which was converted to the sodium salt. $^1$H NMR (300 MHz, DMSO-$d_6$): δ 9.93 (bs, 1H), 7.69-7.67 (m, 1H), 7.63 (d, J=8.6 Hz, 2H), 7.11-7.08 (m, 1H), 7.47 (s, 1H), 7.10 (d, J=8.7 Hz, 2H), 6.91 (d, J=3.9 Hz, 1H), 6.41 (d, J=3.9 Hz, 1H), 3.09-3.02 (m, 2H), 2.70-2.65 (m, 2H). MS m/z: 507 (M+1).

1.2 Preparation of N-(3,3-diphenylpropyl]-N'-[4-(N-thiazol-2-yl-sulfonamyl)-phenyl]-sulfamide Na Salt, 7b

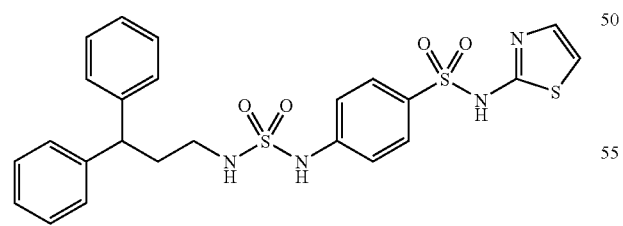

The same procedure was used to prepare 7b, with the exception that 3,3-diphenylpropylamine was used in place of 3,4-dichlorophenethylamine. $^1$H NMR (300 MHz, DMSO-$d_6$): δ 9.94 (bs, 1H), 7.63 (d, J=8.5 Hz, 2H), 7.31-7.11 (m, 10H), 7.06 (d, J=8.7 Hz, 2H), 6.89 (d, J=3.8 Hz, 1H), 6.38 (d, J=3.8 Hz, 1H), 3.95 (t, J=7.6 Hz, 1H), 2.75-2.70 (m, 2H), 2.13 (q, J=6.7 Hz, 2H). MS m/z: 529 (M+1).

1.3 Preparation of N-(trans-2-phenylcyclopropyl)-N'-[4-(N-thiazol-2-yl-sulfonamyl)-phenyl]-sulfamide, 7c

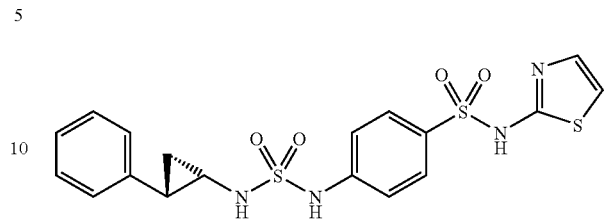

1.3.a Preparation of 2-oxo-oxazolidine-3-sulfonic acid (2-phenyl-cyclopropyl)-amide, 8a

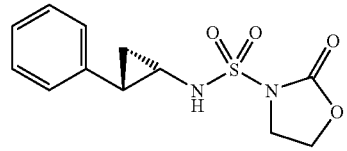

To a round bottom flask was added chlorosulfonyl isocyanate (0.4 mL, 4.64 mmol) and methylene chloride (5 mL) under an atmosphere of argon. The mixture was cooled in an ice bath and 2-bromoethanol (0.535 mL, 7.55 mmol) in methylene chloride (1 mL) was added dropwise. After stirring for 30 minutes at 0° C., triethylamine (2.28 mL, 16.4 mmol) and trans-2-phenylcyclopropylamine hydrochloride (0.867 g, 5.11 mmol), 6a, in methylene chloride (5 mL) was added at such a rate that the reaction temperature was maintained between 0° C. and 10° C. The resulting solution was stirred at rt for 5 h and then partitioned between 1N HCl and water. The organic layer was dried with sodium sulfate, filtered and concentrated. The crude was purified by chromatography to give 569 mg of a waxy solid, 8a.

$^1$H NMR (300 MHz, DMSO-$d_6$): δ 7.34-7.22 (m, 3H), 7.12 (d, J=7.0 Hz, 2H), 6.00 (s, 1H), 4.50-4.33 (m, 2H), 4.16-3.95 (m, 2H), 2.66-2.61 (m, 1H), 2.43-2.37 (m, 1H), 1.48-1.41 (m, 1H), 1.30 (q, J=6.5 Hz, 1H). MS m/z: 283 (M+1).

1.3.b Preparation of N-(trans-2-phenylcyclopropyl)-N'-[4-(N-thiazol-2-yl-sulfonamyl)-phenyl]-sulfamide Na salt, 7c

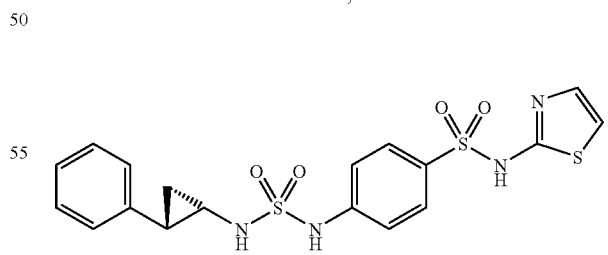

Triethylamine (1.2 mL, 8.7 mmol) and N-(2-thiazolyl)-sulfanilamide (0.285 mL, 1.92 mmol), 4b, were added to a solution of 2-oxo-oxazolidine-3-sulfonic acid (2-phenyl-cyclopropyl)-amide (0.285 mL, 1.92 mmol), 8, in acetonitrile (20 mL). The reaction mixture was heated at 100° C. for 2 h. After cooling to rt, the reaction mixture was concentrated in vacuo. The residue was dissolved in ethyl acetate and washed with 1 N HCl, brine and dried with MgSO$_4$. The crude was purified by column chromatography to give 125.6 mg of 7c. The product was converted to its sodium salt. $^1$H NMR (300 MHz, DMSO-d$_6$): δ 10.1 (bs, 1H), 7.62 (d, J=8.4 Hz, 2H), 7.38-7.14 (m, 3H), 7.08 (d, J=8.6 Hz, 2H), 6.99 (d, J=7.1 Hz, 2H), 6.90 (d, J=3.9 Hz, 1H), 6.39 (d, J=3.9 Hz, 1H), 2.41-2.43 (m, 1H), 1.90-1.84 (m, 1H), 1.07 (q, J=5.9 Hz, 2H). MS m/z: 451 (M+1).

1.4 Preparation of N-[(2,2-diphenyl)]-ethyl]-N'-{2-[5-(N-thiazol-2-yl-sulfonamyl)-pyridinyl]}-sulfamide, 7d

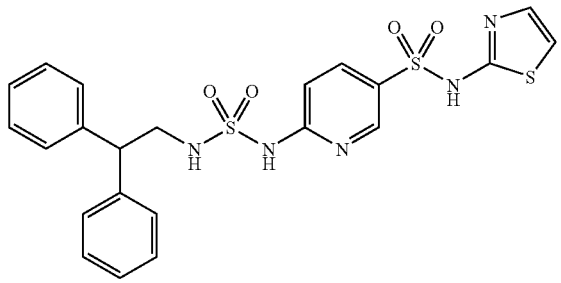

The same procedure was used to prepare compound 7d, with the exception that 6-amino-pyridine-3-sulfonic acid thiaol-2-ylamide was 4-(N-thiazol-2-yl-sulfonamyl)-2-pyridinyl]sulfamide used in place of 4-(N-thiazol-2-yl-sulfonamyl)]-sulfanilamide and 2, 2-diphenylethylamine was used in place of 3,4-dichlorophenethylamine. $^1$H NMR (300 MHz, DMSO-d$_6$): δ 12.86 (1H, bs), 11.10 (1H, bs), 8.5 (1H, d, J=2.4 Hz), 7.95 (1H, dd, J=2.4, 8.7 Hz), 7.53 (1H, t, J=5.5 Hz), 7.11-7.33 (10H, m), 6.97 (1H, d, J=8.8 Hz), 6.89 (1H, d, J=4.6 Hz), 4.16-4.24 (1H, m), 3.52 (2H, t, J=6.2 Hz). MS m/z: 516 (M+1).

1.5 Preparation of N-[(3,3-diphenyl)]-propyl]-N'-{5-[5-(N-thiazol-2-yl-sulfonamyl)-pyridinyl]}-sulfamide, 7e

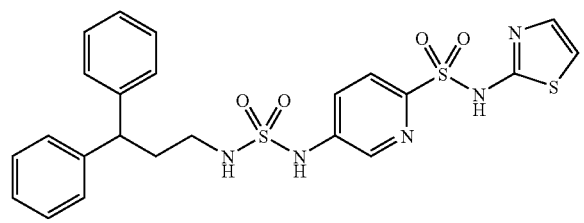

The same procedure was used to prepare compound 7e, with the exception that 5-amino-pyridine-2-sulfonic acid thiaol-2-ylamide was used in place of 6-amino-pyridine-3-sulfonic acid thiaol-2-ylamide and 2,2-diphenylethylamine was used in place of 3,4-dichlorophenethylamine. $^1$H NMR (300 MHz, DMSO-d$_6$): δ 12.77 (1H, bs), 10.42 (1H, s), 8.34 (1H, d, J=2.5 Hz), 7.89-7.94 (2H, m), 7.63 (1H, dd, J=2.5, 8.6 Hz), 7.11-7.30 (10H, m), 6.85 (1H, d, J=4.6 Hz), 3.93 (1H, t, J=7.8 Hz), 2.75 (2H, q, J=6.4 Hz), 2.15 (2H, d, J=7.3 Hz). MS m/z: 530 (M+1).

Example 2

2.1 Preparation of benzene-1,4-disulfonic acid 1-[(2,2-diphenylethyl)-amide]4-thiazol-2-ylamide, 10a

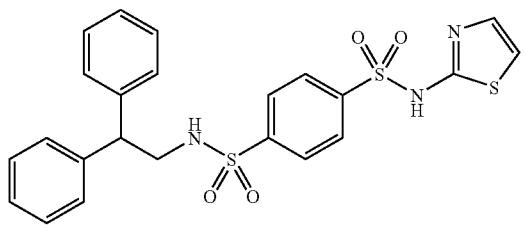

2.1.a Preparation of 4-(thiazol-2-ylsulfamoyl)-benzenesulfonyl chloride, 9a

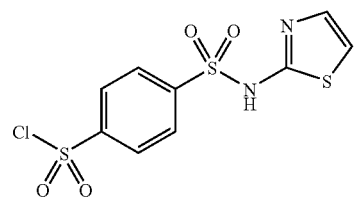

To a mixture of N-(2-thiazolyl)-sulfanilamide (1.27 g, 4.97 mmol), 4a, in acetonitrile (40 mL) was added acetic acid (4 mL), followed by concentrated hydrogen chloride (4 mL). The resulting slurry was cooled to 5° C. and sodium nitrite (0.38 g, 5.5 mmol) in 1 mL of water was added over and the mixture was stirred. After 20 min the slurry became a clear orange solution and then SO$_2$ in acetic acid (10 mL) was added followed by copper (II) chloride (0.67 g, 5.0 mmol) in 1 mL of water. The mixture was stirred for 2 h and the yellow precipitate was filtered, washed with acetonitrile, water, and dried overnight to give the desired product 9a as a yellow solid. MS m/z: 339 (M+1).

2.1.b Preparation of benzene-1,4-disulfonic acid 1-[(2,2-diphenyl-ethyl)-amide]4-thiazol-2-ylamide, 10a

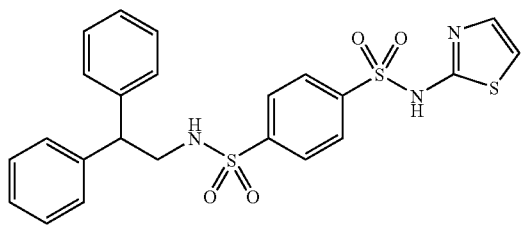

To a vial was added 4-(thiazol-2-ylsulfamoyl)-benzenesulfonyl chloride 9a (0.105 g, 0.3 mmol), pyridine (1 mL), and 2,2-diphenyl-ethylamine (0.0640 g, 0.3 mmol). The reaction was stirred overnight and then concentrated. The crude product was purified by chromatography to give desired compound 10a. MS m/z: 500 (M+1).

2.2.a Preparation of benzene-1,4-disulfonic acid 1-[(2,2-diphenyl-ethyl)-amide]4-thiazol-2-ylamide, 10b The same procedure was used to prepare compound 10a, with the exception that 2-phenylethylamine -was used in place of 2,2-diphenylethylamine. MS m/z: 430 (M+1).

Example 3

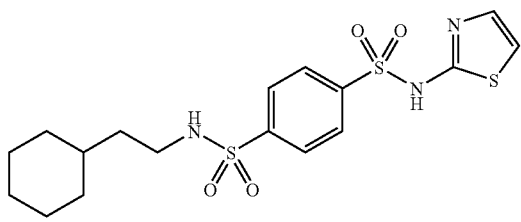

Example 3 provides methods for testing the efficacy of the compounds of the invention.

3.1.a Cell Line Construction and Maintenance

Human Embryonic Kidney (HEK) cells were transfected with an hSCN3A construct using lipofectamine reagent (Invitrogen), using standard techniques. Cells stably expressing the hSCN3A constructs were identified by their resistance to G-418 (400 µg/ml). Clones were screened for expression using the whole-cell voltage-clamp technique.

3.2.a Cell Culture

HLK cells stably transfected with hSCN3A were maintained in DMEM medium supplemented with 10% heat-inactivated fetal bovine serum and 400 µg/ml G418 sulfate in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and replated at low density onto glass cover slips. Cells were typically used for electrophysiological experiments within 24 to 72 h after plating.

3.3.a Electrophysiological Recording

Cover slips containing HEK cells expressing hSCN3A were placed in a bath on the stage of an inverted microscope and perfused (approximately 1 ml/min) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 to 7.4, and had a resistance of 1 to 2 mega ohms. The osmolarity of the extracellular and intracellular solutions was 300 mmol/kg and 295 mmol/kg, respectively. All recordings were made at room temperature (22-24° C.) using AXOPATCH 200B amplifiers and PCLAMP software (Axon Instruments, Burlingame, Calif.) or PatchXpress 7000 hardware and associated software (Axon Instruments, Burlingame, Calif.).

hSCN3A currents in HEK cells were measured using the whole-cell configuration of the patch-clamp technique (Hamill et al., 1981). Uncompensated series resistance was typically 2 to 5 mega ohms and >85% series resistance compensation (50% for PatchXpress) was routinely achieved. As a result, voltage errors were negligible and no correction was applied. Current records were acquired at 20 to 50 KHz and filtered at 5 to 10 KHz.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage midpoint of inactivation ($V_{1/2}$). Cells were then voltage clamped at the empirically determined $V_{1/2}$.

Compounds were tested for their ability to inhibit hSCN3A sodium channels by activating the channel with a 20 ms voltage step to 0 mV from the empirically determined $V_{1/2}$. HEK cells stably transfected with hSCN3A were viewed under Hoffman contrast optics and placed in front of an array of flow pipes emitting either control or compound-containing extracellular solutions. In the cases where data were generated on the PatchXpress the onboard liquid handling facility of the instrument was used. All the compounds were dissolved in dimethyl sulfoxide to make 10 mM stock solutions, which were then diluted into bath solution to attain the final concentrations desired. The final concentration of dimethyl sulfoxide ($\leq$1% dimethyl sulfoxide) was found to have no significant effect on hSCN3A sodium currents.

3.4.a High-Throughput Screening Assays

Confluent cells in multi-well plates were incubated with a permeant radioactive ion ($^{22}$Na, $^{14}$C-guanidinium, etc) for 4-16 hours to allow uptake of the radiotracer. Excess radioactive ions were removed by washing with prewarmed buffer of the following composition: 138 mM NaCl, 2 mM $CaCl_2$, 5.4 mM KCl, 1 mM $MgCl_2$, 10 mM glucose, and 10 mM HEPES, pH 7.4, with NaOH. Efflux was initiated by addition of buffer containing any necessary chemical activators (e.g., 100 µM veratridine, 10-20 µg/ml Lqh scorpion venom, etc.). Various concentrations of test compounds or reference sodium channel blockers were added concurrently with the initiation of efflux. Efflux was allowed to progress for a defined period of time, typically 30-90 minutes, at 37° C. in a humidified 10% $CO_2$ atmosphere. Stimulated efflux was determined by collecting the extracellular solution and transferring to a multiwell plate for scintillation counting. Residual intracellular radioactivity was also determined by scintillation counting following lysis of the cells in the assay plate. Inhibition of efflux was determined by comparing efflux in the presence of test compounds to efflux in untreated control cells.

The activity of certain compounds of the present invention is set forth in Table II, below.

TABLE II

| Compound Number | NAME | SCN3A Inhibitory Activity |
|---|---|---|
| 1 | N-[(2,2-diphenyl)]-ethyl]-N'-[4-(N-thiazol-2-yl-sulfonamyl)-phenyl]-sulfamide | ++++ |
| 2 | N-(3,3-diphenylpropyl)-N'-[4-(N-thiazol-2-yl-sulfonamyl)-phenyl]-sulfamide | ++++ |
| 3 | N-(3,4-dichloro-phenyl)-ethyl]-N'-[4-(N-thiazol-2-yl-sulfonamyl)-phenyl]-sulfamide | ++++ |
| 4 | N-(trans-2-phenylcyclopropyl)-N'-[4-(N-thiazol-2-yl-sulfonamyl)-phenyl]-sulfamide | ++++ |
| 5 | N-[2-(4-phenoxyl-phenyl)-ethyl]-N'-[4-(N-thiazol-2-yl-sulfonamyl)-phenyl]-sulfamide | ++++ |
| 6 | Benzene-1,4-disulfonic acid 1-{[2-(4-tert-butyl-phenoxy)-ethyl]-amide} 4-[(5-chloro-thiazol-2-yl)-amide] | ++++ |
| 7 | Benzene-1,4-disulfonic acid 1-[(5-chloro-thiazol-2-yl)-amide] 4-[(3,3-dimethyl-butyl)-amide] | ++++ |
| 8 | 4-[4-(3-Chloro-phenoxy)-piperidine-1-sulfonyl]-N-thiazol-2-yl-benzenesulfonamide | ++++ |
| 9 | Benzene-1,4-disulfonic acid 1-[(6,7-dichloro-2,3-dihydro-benzo[1,4]dioxin-2-ylmethyl)-amide] 4-thiazol-2-ylamide | ++++ |
| 10 | 4-[4-(4-Chloro-2-fluoro-phenyl)-piperazine-1-sulfonyl]-N-(5-chloro-thiazol-2-yl)-benzenesulfonamide | ++++ |
| 11 | Benzene-1,4-disulfonic acid 1-(4-tert-butyl-benzylamide) 4-thiazol-2-ylamide | ++++ |
| 12 | Benzene-1,4-disulfonic acid 1-{[3-(4-chloro-phenoxy)-propyl]-amide} 4-[(5-chloro-thiazol-2-yl)-amide] | ++++ |
| 13 | Benzene-1,4-disulfonic acid 1-({2-[(4-chloro-phenyl)-methyl-amino]-ethyl}-amide) 4-thiazol-2-ylamide | ++++ |
| 14 | Benzene-1,4-disulfonic acid 1-{[2-(4-tert-butyl-phenoxy)-2-methyl-propyl]-amide} 4-[(5-chloro-thiazol-2-yl)-amide] | ++++ |
| 15 | Benzene-1,4-disulfonic acid 1-[(5-chloro-thiazol-2-yl)-amide] 4-(4-trifluoromethyl-benzylamide) | ++++ |
| 16 | Benzene-1,4-disulfonic acid 1-{[2-(4-tert-butyl-phenylamino)-ethyl]-amide} 4-thiazol-2-ylamide | ++++ |
| 17 | Benzene-1,4-disulfonic acid 1-{[1-(4-chloro-phenoxy)-cyclobutylmethyl]-amide} 4-thiazol-2-ylamide | ++++ |
| 18 | Benzene-1,4-disulfonic acid 1-{[2-(4-chloro-3-methyl-phenoxy)-ethyl]-amide} 4-thiazol-2-ylamide | ++++ |
| 19 | 4-[(S)-2-(4-chloro-phenoxymethyl)-pyrrolidine-1-sulfonyl]-N-thiazol-2-yl-benzenesulfonamide | ++++ |
| 20 | Benzene-1,4-disulfonic acid 1-{[1-(4-chloro-2-fluoro-phenoxy)-cyclobutylmethyl]-amide} 4-thiazol-2-ylamide | ++++ |
| 21 | Benzene-1,4-disulfonic acid 1-{[1-(4-chloro-phenyl)-cyclobutylmethyl]-amide} 4-thiazol-2-ylamide | ++++ |
| 22 | N-[(3,3-diphenyl)]-propyl]-N'-{5-[5-(N-thiazol-2-yl-sulfonamyl)-pyridinyl]}-sulfamide | +++ |
| 23 | 4-(3,4-Dichloro-phenyl)-piperazine-1-sulfonic acid [4-(thiazol-2-ylsulfamoyl)-phenyl]-amide | +++ |
| 24 | Benzene-1,4-disulfonic acid 1-[(2,2-diphenyl-ethyl)-amide] 4-thiazol-2-ylamide | +++ |
| 25 | 2,5-Difluoro-benzene-1,4-disulfonic acid 1-{[2-(3,4-dichloro-phenyl)-ethyl]-amide} 4-thiazol-2-ylamide | +++ |
| 26 | N-(5-chloro-thiazol-2-yl)-4-[3-(3-chloro-5-trifluoromethyl-pyridin-2-yloxy)-azetidine-1-sulfonyl]-benzenesulfonamide | +++ |
| 27 | Benzene-1,4-disulfonic acid 1-{[2-(4-chloro-phenyl)-ethyl]-amide} 4-thiazol-2-ylamide | +++ |
| 28 | N-(5-chloro-thiazol-2-yl)-4-[3-(3,4-dichloro-benzylidene)-azetidine-1-sulfonyl]-benzenesulfonamide | +++ |
| 29 | 4-[4-(4-Chloro-benzyl)-piperidine-1-sulfonyl]-N-thiazol-2-yl-benzenesulfonamide | +++ |
| 30 | Benzene-1,4-disulfonic acid 1-cycloheptylamide 4-thiazol-2-ylamide | +++ |
| 31 | Benzene-1,4-disulfonic acid 1-{[2-(4-tert-butyl-phenylamino)-2-methyl-propyl]-amide} 4-thiazol-2-ylamide | +++ |
| 32 | Benzene-1,4-disulfonic acid 1-{[(R)-2-(4-chloro-phenoxy)-propyl]-amide} 4-[(5-chloro-thiazol-2-yl)-amide] | +++ |
| 33 | Benzene-1,4-disulfonic acid 1-{[(S)-2-(4-chloro-phenoxy)-propyl]-amide} 4-[(5-chloro-thiazol-2-yl)-amide] | +++ |
| 34 | Benzene-1,4-disulfonic acid 1-{[2-(4-chloro-2-fluoro-phenoxy)-ethyl]-amide} 4-thiazol-2-ylamide | +++ |
| 35 | Benzene-1,4-disulfonic acid 1-{[2-(4-tert-butyl-phenoxy)-ethyl]-methyl-amide} 4-thiazol-2-ylamide | +++ |
| 36 | 4-[3-(3-Chloro-phenoxymethyl)-azetidine-1-sulfonyl]-N-thiazol-2-yl-benzenesulfonamide | +++ |
| 37 | Benzene-1,4-disulfonic acid 1-(3-chloro-4-methoxy-benzylamide) 4-thiazol-2-ylamide | +++ |
| 38 | Benzene-1,4-disulfonic acid 1-{[1-(4-tert-butyl-phenoxy)-cyclopentylmethyl]-amide} 4-thiazol-2-ylamide | +++ |

TABLE II-continued

| Compound Number | NAME | SCN3A Inhibitory Activity |
|---|---|---|
| 39 | Benzene-1,4-disulfonic acid 1-{[2-(4-chloro-phenyl)-2-methyl-propyl]-amide} 4-thiazol-2-ylamide | +++ |
| 40 | Benzene-1,4-disulfonic acid 1-(3-fluoro-5-trifluoromethyl-benzylamide) 4-thiazol-2-ylamide | +++ |
| 41 | Benzene-1,4-disulfonic acid 1-{[2-(5-chloro-thiophen-2-yl)-ethyl]-amide} 4-thiazol-2-ylamide | +++ |
| 42 | 2-Fluoro-benzene-1,4-disulfonic acid 4-[(3,3-dimethyl-butyl)-amide] 1-thiazol-2-ylamide | +++ |
| 43 | N-[2-(2-chloro-phenoxyl)-ethyl]-N'-[4-(N-thiazol-2-yl-sulfonamyl)-phenyl]-sulfamide | ++ |
| 44 | Benzene-1,4-disulfonic acid 1-[(2-cyclohexyl-ethyl)-amide] 4-thiazol-2-ylamide | ++ |
| 45 | N-[(2,2-diphenyl)]-ethyl]-N'-{2-[5-(N-thiazol-2-yl-sulfonamyl)-pyridinyl]}-sulfamide | + |
| 46 | N-[2-(4-tetrahydro-pyranyl)-ethyl]-N'-[4-(N-thiazol-2-yl-sulfonamyl)-phenyl]-sulfamide | + |
| 47 | Benzene-1,4-disulfonic acid 1-(methyl-phenethyl-amide) 4-thiazol-2-ylamide | + |

Key:
+ indicates IC50 > 1 µM;
++ indicates 1 µM > IC50 > 0.5 µM;
+++ indicates 0.5 µM > IC50 > 0.1 µM;
++++ indicates IC50 < 0.1 µM While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in their entirety.

What is claimed is:

1. A compound according to Formula I:

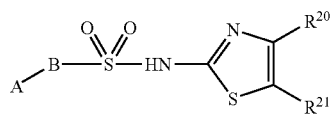

(I)

wherein
A is

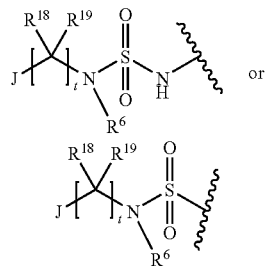

wherein
$R^{18}$ and $R^{19}$ are each independently selected from H, unsubstituted alkyl or phenyl; or $R^{18}$ and $R^{19}$, together with the carbon atoms to which they are attached, are joined to form an unsubstituted cycloalkyl;

the subscript t is an integer selected from 1 to 4;

J is a member selected from phenyl, phenoxy, phenylamino, cyclohexyl, cycloheptyl, tetrahydropyranyl, benzodioxanyl, thiophenyl, pyridinoxy or homoalkyl, wherein the aromatic portion of which is optionally substituted with from one to two members selected from phenoxy, homoalkyl, homoalky-oxy, halogen or halo-homoalkyl;

$R^6$ is H or; $R^6$ and $R^{18}$ together with the atoms to which $R^6$ and $R^{18}$ are attached, are optionally joined to form an azetidinyl, piperidinyl, pyrrolidinyl or piperazinyl moiety;

B is a member selected from:

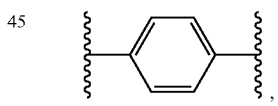 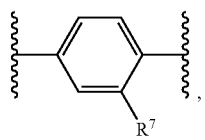

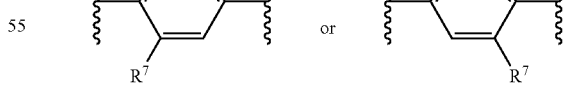

wherein
$R^7$ is a -cyano, halogen, or $CF_3$;
$R^{20}$ and $R^{21}$ are members independently selected from H, halogen or homoalkyl; or
a pharmaceutically acceptable salt thereof.

2. The compound of claim 1, which has a formula which is a member selected from:

US 7,705,158 B2

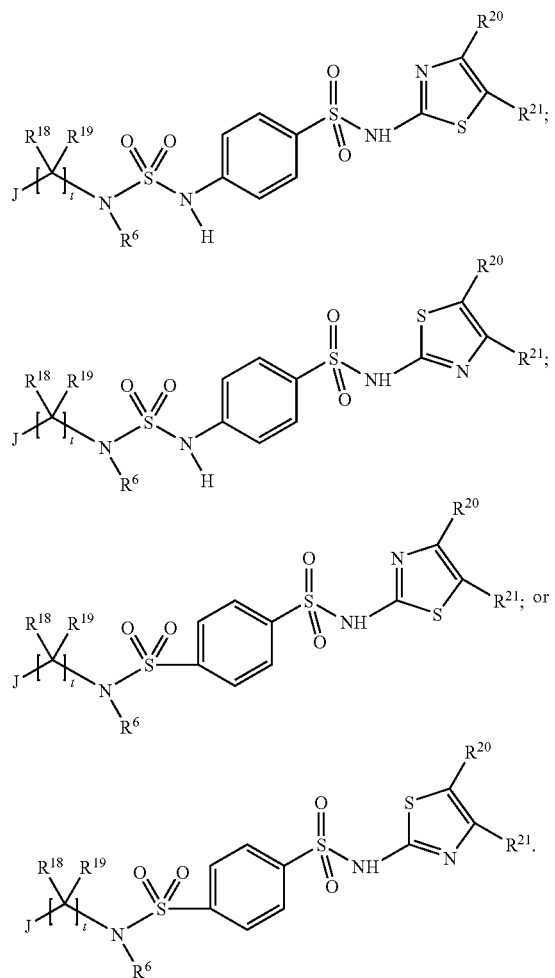

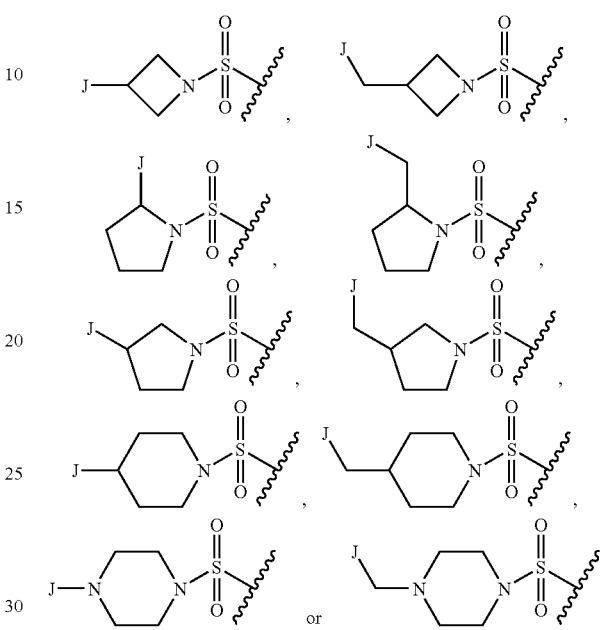

3. A pharmaceutical formulation comprising the compound of claim 1 or a pharmaceutically acceptable salt thereof and a pharmaceutically acceptable excipient.

4. The compound of claim 1, wherein $R^7$ is —F or halogen.

5. The compound of claim 2, wherein $R^{20}$ and $R^{21}$ are each independently selected from H and halogen.

6. The compound of claim 5, wherein $R^{20}$ and $R^{21}$ are each independently selected from H or halogen;

$R^{18}$ and $R^{19}$ are each independently selected from H, phenyl or unsubstituted alkyl; or $R^{18}$ and $R^{19}$ together with the carbon atoms to which they are attached, are joined to form a cyclopropyl, cyclobutyl, cyclopentyl or cyclohexyl ring; and J is selected from phenyl, phenoxy, phenylamino, cyclohexyl, cycloheptyl, tetrahydropyranyl, benzodioxanyl, thiophenyl, pyridinoxy or homoalkyl, wherein the aromatic portion of which is optionally substituted with from one to two members independently selected from halogen, methyl, trifluoromethyl, ethyl, t-butyl, or methoxy.

7. The compound of claim 6, wherein J is phenyl, phenyloxy, phenylamino, pyridinoxy or benzo[1,4]dioxin-2-yl, wherein the aromatic portion of which is optionally substituted with from one to two members independently selected from halogen, methyl, trifluoromethyl, ethyl, t-butyl, or methoxy.

8. The compound of claim 4, wherein A is a member selected from:

wherein J is selected from the group consisting of phenyl, phenoxy, phenylamino, cyclohexyl, cycloheptyl, tetrahydropyranyl, benzodioxanyl, thiophenyl, pyridinoxy or homoalkyl, wherein the aromatic portion of which is optionally substituted with from one to two members independently selected from the group consisting of halogen, methyl, trifluoromethyl, ethyl, t-butyl and methoxy.

9. The compound of claim 8, wherein J is selected from the group consisting of phenyl, phenyloxy, phenylamino and pyridinyloxy, wherein aromatic portion of which is optionally substituted with from one to two members independently selected from the group consisting of halogen, methyl, trifluoromethyl, ethyl, t-butyl and methoxy.

10. The compound of claim 9, wherein J is phenyl optionally substituted with from one to two members independently selected from the group consisting of halogen, methyl, trifluoromethyl, ethyl, t-butyl and methoxy.

11. The compound of claim 10, wherein J is chlorophenyl, fluorophenyl, dichlorophenyl, difluorophenyl, chlorofluorophenyl, trifluoromethylfluorophenyl, trifluoromethylchlorophenyl, t-butylchlorophenyl, t-butylfluorophenyl, methylchlorophenyl, methylfluorophenyl, methoxychlorophenyl or methoxyfluorophenyl.

12. The compound of claim 9, wherein J is phenoxy optionally substituted with from one to two members independently selected from the group consisting of halogen, methyl, trifluoromethyl, ethyl, t-butyl and methoxy.

13. The compound of claim 12, wherein J is chlorophenoxy, fluorophenoxy, dichlorophenoxy, difluorophenoxy, chlorofluorophenoxy, trifluoromethylfluorophenoxy, trifluoromethylchlorophenoxy, t-butylchlorophenoxy, t-butylfluorophenoxy, methylchlorophenoxy, methylfluorophenoxy, methoxychlorophenoxy or methoxyfluorophenoxy.

14. The compound of claim 9, wherein J is phenylamino optionally substituted with from one to two members independently selected from the group consisting of halogen, methyl, trifluoromethyl, ethyl, t-butyl and methoxy.

15. The compound of claim 14, wherein J is chlorophenylamino, fluorophenylamino, dichlorophenylamino, difluorophenylamino, chlorofluorophenylamino, trifluoromethylfluorophenylamino, trifluoromethylchlorophenylamino, t-butylchlorophenylamino, t-butylfluorophenylamino, methylchlorophenylamino, methylfluorophenylamino, methoxychlorophenylamino or methoxyfluorophenylamino.

16. The compound of claim 9, wherein J is pyridinyloxy optionally substituted with from one to two members independently selected from the group consisting of halogen, methyl, trifluoromethyl, ethyl, t-butyl and methoxy.

17. The compound of claim 16, wherein J is selected from chloropyridinyloxy, fluoropyridinyloxy, dichloropyridinyloxy, difluoropyridinyloxy, chlorofluoropyridinyloxy, trifluoromethylfluoro pyridinyloxy, trifluoromethylchloropyridinyloxy, t-butylchloropyridinyloxy, t-butylfluoropyridinyloxy, methylchloropyridinyloxy, methylfluoropyridinyloxy, methoxychloropyridinyloxy or methoxyfluoropyridinyloxy.

18. A compound having the formula:

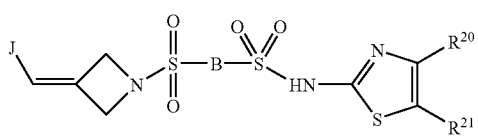

wherein J is selected from phenyl, phenoxy, phenylamino, cyclohexyl, cycloheptyl, tetrahydropyranyl, benzodioxanyl, thiophenyl, pyridinoxy or homoalkyl, wherein the aromatic portion of which is optionally substituted with from one to two members selected from phenoxy, homoalkyl, homoalkyoxy, halogen or halo-homoalkyl;

B is a member selected from:

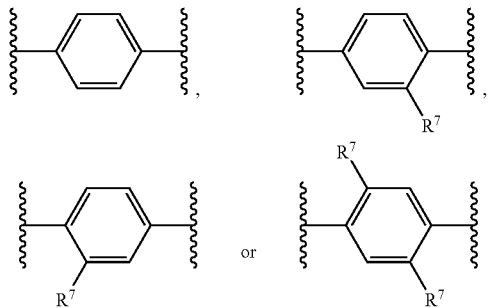

wherein $R^7$ is H, F or halogen; and
$R^{20}$ and $R^{21}$ are members independently selected from H, halogen or homoalkyl.

19. The compound of claim 18, wherein J is phenyl optionally substituted with from one to two members independently selected from the group consisting of halogen, methyl, trifluoromethyl, ethyl, t-butyl and methoxy.

20. The compound of claim 19, wherein J is chlorophenyl, fluorophenyl, dichlorophenyl, difluorophenyl, chlorofluorophenyl, trifluoromethylfluorophenyl, trifluoromethylchlorophenyl, t-butylchlorophenyl, t-butylfluorophenyl, methylchlorophenyl, methylfluorophenyl, methoxychlorophenyl or methoxyfluorophenyl.

21. The compound of claim 4, wherein A is a member selected from:

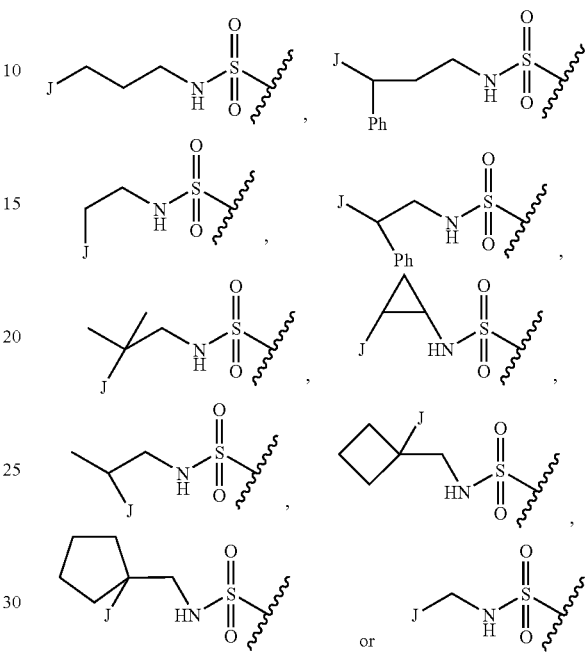

wherein J is selected from the group consisting of phenyl, phenoxy, phenylamino, cyclohexyl, cycloheptyl, tetrahydropyranyl, benzodioxanyl, thiophenyl, pyridinoxy or homoalkyl, wherein the aromatic portion of which is optionally substituted with from one to two members independently selected from the group consisting of halogen, methyl, trifluoromethyl, ethyl, t-butyl and methoxy.

22. The compound of claim 21, wherein J is selected from the group consisting of methyl, ethyl, propyl, 3,3-dimethylbutyl, phenyl, phenyloxy and phenylamino, wherein the phenyl moiety is optionally substituted with from one to two members independently selected from the group consisting of halogen, methyl, trifluoromethyl, ethyl, t-butyl and methoxy.

23. The compound of claim 22, wherein J is phenyl optionally substituted with from one to two members independently selected from the group consisting of halogen, methyl, trifluoromethyl, ethyl, t-butyl and methoxy.

24. The compound of claim 23, wherein J is chlorophenyl, fluorophenyl, dichlorophenyl, difluorophenyl, chlorofluorophenyl, trifluoromethylfluorophenyl, trifluoromethylchlorophenyl, t-butylchlorophenyl, t-butylfluorophenyl, methylchlorophenyl, methylfluorophenyl, methoxychlorophenyl or methoxyfluorophenyl.

25. The compound of claim 22, wherein J is phenoxy optionally substituted with from one to two members independently selected from the group consisting of halogen, methyl, trifluoromethyl, ethyl, t-butyl and methoxy.

26. The compound of claim 25, wherein J is chlorophenoxy, fluorophenoxy, dichlorophenoxy, difluorophenoxy, chlorofluorophenoxy, trifluoromethylfluorophenoxy, trifluoromethylchlorophenoxy, t-butylchlorophenoxy, t-butylfluorophenoxy, methylchlorophenoxy, methylfluorophenoxy, methoxychlorophenoxy or methoxyfluorophenoxy.

27. The compound of claim 22, wherein J is phenylamino optionally substituted with from one to two members independently selected from the group consisting of halogen, methyl, trifluoromethyl, ethyl, t-butyl and methoxy.

28. The compound of claim 27, wherein J is chlorophenylamino, fluorophenylamino, dichlorophenylamino, difluorophenylamino, chlorofluorophenylamino, trifluoromethylfluorophenylamino, trifluoromethylchlorophenylamino, t-butylchlorophenylamino, t-butylfluorophenylamino, methylchlorophenylamino, methylfluorophenylamino, methoxychlorophenylamino or methoxyflurophenylamino.

29. The compound of claim 4, wherein J is benzo[1,4]dioxin-2-yl, wherein the phenyl is optionally substituted with from one to two members independently selected from halogen, methyl, trifluoromethyl, ethyl, t-butyl, or methoxy.

30. The compound of claim 29, wherein J is selected from the group consisting of chlorobenzo[1,4]dioxin-2-yl, fluorobenzo[1,4]dioxin-2-yl, dichlorobenzo[1,4]dioxin-2-yl, difluorobenzo[1,4]dioxin-2-yl, chlorofluorobenzo[1,4]dioxin-2-yl, trifluoromethylfluorobenzo[1,4]dioxin-2-yl, trifluoromethylchlorobenzo[1,4]dioxin-2-yl, t-butylchlorobenzo [1,4]dioxin-2-yl, t-butylfluorobenzo[1,4]dioxin-2-yl, methylchlorobenzo[1,4]dioxin-2-yl, methylfluorobenzo[1,4]dioxin-2-yl, methoxychlorobenzo[1,4]dioxin-2-yl and methoxyfluorobenzo[1,4]dioxin-2-yl.

31. The compound of claim 1, wherein the compound is selected from the group consisting of:
N-[(2,2-diphenyl)]-ethyl]-N'-[4-(N-thiazol-2-yl-sulfonamyl)-phenyl]- sulfamide;
N-(3,3-diphenylpropyl]-N'-[4-(N-thiazol-2-yl-sulfonamyl)-phenyl ]-sulfamide;
N-(3,4dichloro-phenyl)-ethyl]-N'-[4-(N-thiazol-2-yl-sulfonamyl)-phenyl-]-sulfamide;
N-(trans-2-phenylcyclopropyl)-N'-[4-(N-thiazol-2-yl-sulfonamyl)-phenyl]-sulfamide;
N-[2-(4-phenoxyl-phenyl)-ethyl]-N'-[4(N-thiazol-2-yl-sulfonamyl)-pheny-1]-sulfamide;
Benzene-1,4-disulfonic acid 1-{[2-(4-tert-butyl-phenoxy)-ethyl]-amide}4-[(5-chloro-thiazol-2-yl)-amide];
Benzene-1,4-disulfonic acid 1-[(5-chloro-thiazol-2-yl)-amide]4-[(3,3-dimethyl-butyl)-amide];
4-[4-(3-Chloro-phenoxy)-piperidine-1-sulfonyl]-N-thiazol-2-yl-benzenesulfonamide;
Benzene-1,4-disulfonic acid 1-[(6,7-dichloro-2,3-dihydro-benzo[1,4]dioxin-2-ylmethyl)-amide]4-thiazol-2-ylamide;
4-[4-(4-Chloro-2-fluoro-phenyl)-piperazine-1sulfony]-N-(5-chloro-thiazol-2-yl )-benzenesulfonamide;
Benzene-1,4-disulfonic acid 1-(4-tert-butyl-benzylamide) 4-thiazol-2-ylamide;
Benzene-1,4-disulfonic acid 1-{[3-(4-chloro-phenoxy)-propyl]-amide}4-[(5-chloro-thiazol-2-yl)-amide];
Benzene-1,4-disulfonic acid 1-({2-[(4-chloro-phenyl)-methyl-amino]-ethyl}-amide) 4-thiazol-2-ylamide;
Benzene-1,4-disulfonic acid 1-{[2-(4-tert-butyl-phenoxy)-2-methyl-propyl]-amide }4-[(5-chloro-thiazol-2-yl)-amide];
Benzene-1,4-disulfonic acid 1-[(5-chloro-thiazol-2-yl)-amide]4-(4-trifluoromethyl-benzylamide);
Benzene-1,4-disulfonic acid 1-{[2-(4-tert-butyl-phenylamino)-ethyl]-amide}4-thiazol-2-ylamide;
Benzene-1,4-disulfonic acid 1-{[1-(4-chloro-phenoxy)-cyclobutylmethyl]-amide }4-thiazol-2-ylamide;
Benzene-1,4-disulfonic acid 1-{[2-(4-chloro-3-methyl-phenoxy)-ethyl-amide}4-thiazol-2-ylamide;
4-[(S)-2-(4-chloro-phenoxymethyl)-pyrrolidine-1-sulfonyl]-N-thiazol-2-y-1-benzenesulfonamide;
Benzene-1,4-disulfonic acid 1-{[1-(4-chloro-2-fluoro-phenoxy)-cyclobutylmethyl ]-amide}4-thiazol-2-ylamide;
Benzene-1,4-disulfonic acid 1-{[1(4-chloro-phenyl)-cyclobutylmethyl]-amide}4-thiazol-2-ylamide;
N-[(3,3-diphenyl)]-propyl]-N'-{5-[5-(N-thiazol-2-yl-sulfonamyl)-pyridinyl]}-sulfamide;
4-(3,4-Dichloro-phenyl)-piperazine-1-sulfonic acid [4-(thiazol-2-ylsulfamoyl)-phenyl ]-amide;
Benzene-1,4-disulfonic acid 1-[(2,2-diphenyl-ethyl)-amide]4-thiazol-2-ylamide;
2,5-Difluoro-benzene1,4-disulfonic acid 1-{[2-(3,4-dichloro-phenyl)-ethyl]-amide }4-thiazol-2-ylamide;
N-(5-chloro-thiazol-2-yl)-4-[3-(3-chloro-5-trifluoromethyl-pyridin-2-yl-oxy)-azetidine-1-sulfonyl]-benzenesulfonamide;
Benzene-1,4-disulfonic acid 1-{[2-(4-chloro-phenyl)-ethyl]-amide}4-thiazol-2-ylamide;
N-(5-chloro-thiazol-2-yl)-4-[3-(3,4-dichloro-benzylidene)-azetidine-1-sulfonyl]-benzenesulfonamide;
4-[4-(4-Chloro-benzyl)-piperidine-1-sulfonyl]-N-thiazol-2-yl-benzenesulfonamide;
Benzene-1,4-disulfonic acid 1-cycloheptylamide 4-thiazol-2-ylamide;
Benzene-1,4-disulfonic acid 1-{[2-(4-tert-butyl-phenylamino)-2-methyl-propyl]-amide }4-thiazol-2-ylamide;
Benzene-1,4-disulfonic acid 1-{[(R)-2-(4-chloro-phenoxy)-propyl]-amide}4-[(5-chloro-thiazol-2-yl)-amide];
Benzene-1,4-disulfonic acid 1-{[(S)-2-(4-chloro-phenoxy)-propyl]-amide}4-[(5-chloro-thiazol-2-yl)-amide];
Benzene-1,4-disulfonic acid 1-{[2-(4-chloro-2-fluoro-phenoxy)-ethyl]-amide}4-thiazol-2-ylamide;
Benzene-1,4-disulfonic acid 1-{[2-(4-tert-butyl-phenoxy)-ethyl]-methyl-amide}4-thiazol-2-ylamide;
4-[3-(3-Chloro-phenoxymethyl)-azetidine-1-sulfonyl]-N-thiazol-2-yl-benzenesulfonamide;
Benzene-1,4-disulfonic acid 1-(3-chloro-4-methoxy-benzylamide)4-thiazol-2-ylamide;
Benzene-1,4-disulfonic acid 1-{[1-(4-tert-butyl-phenoxy)-cyclopentylmethyl]-amide }4-thiazol-2-ylamide;
Benzene-1,4-disulfonic acid 1-{[2-(4-chloro-phenyl)-2-methyl-propyl]-amide}4-thiazol-2-ylamide;
Benzene-1,4-disulfonic acid 1-(3-fluoro-5-trifluoromethyl-benzylamide)4-thiazol-2-ylamide;
Benzene-1,4-disulfonic acid 1-{[2-(5-chloro-thiophen-2-yl)-ethyl]-amide}4-thiazol-2-ylamide;
2-Fluoro-benzene-1,4-disulfonic acid 4-[(3,3-dimethyl-butyl)-amide]1-thiazol-2-ylamide;
N-[2-(2-chloro-phenoxyl)-ethyl]-N'-[4-(N-thiazol-2-yl-sulfonamyl)-pheny-1]-sulfamide;
Benzene-1,4-disulfonic acid 1-[(2-cyclohexyl-ethyl)-amide]4-thiazol-2-ylamide;
N-[(2,2-diphenyl)]-ethyl]-N'-{2-[5-(N-thiazol-2-yl-sulfonamyl)-pyridiny-1]}-sulfamide; and
N-[2-(4-tetrahydro-pyranyl)-ethyl]-N'-[4-(N-thiazol-2-yl-sulfonamyl)-phenyl]-sulfamide;.

* * * * *

UNITED STATES PATENT AND TRADEMARK OFFICE
CERTIFICATE OF CORRECTION

PATENT NO. : 7,705,158 B2  Page 1 of 1
APPLICATION NO. : 11/555977
DATED : April 27, 2010
INVENTOR(S) : Wang et al.

It is certified that error appears in the above-identified patent and that said Letters Patent is hereby corrected as shown below:

In claim 1, column 44, line 36, please delete ";" after "or" and insert a --;-- after "H" in column 44, line 36.

In claim 31, column 49, line 32, please delete "(3,4dichloro-phenyl)" and insert --(3,4-dichloro-phenyl)--.

In claim 31, column 49, line 48, please delete "1sulfony" and insert --1-sulfonyl--.

In claim 31, column 50, line 2, please delete "ethyl" and insert --ethyl]--

In claim 31, column 50, line 16, please delete "benzene1,4" and insert --benzene-1,4--.

In claim 31, column 50, line 57, please delete "pheny-1" and insert --phenyl--.

In claim 31, column 50, line 61, please delete "pyridiny-1" and insert --pyridinyl--.

In claim 31, column 50, line 63, please delete ";" before the final period.

Signed and Sealed this

Twenty-first Day of December, 2010

David J. Kappos
*Director of the United States Patent and Trademark Office*